United States Patent
Andrews et al.

(10) Patent No.: US 8,637,610 B2
(45) Date of Patent: Jan. 28, 2014

(54) CROSSLINKED POLYMERS CONTAINING BIOMASS DERIVED MATERIALS

(71) Applicant: E I Du Pont De Nemours and Company, Wilmington, DE (US)

(72) Inventors: Mark Allen Andrews, Wilmington, DE (US); Garret D Figuly, Wilmington, DE (US); Henry Keith Chenault, Hockessin, DE (US)

(73) Assignee: E I du Pont de Nemours and Company, Wilmington, DE (US)

( * ) Notice: Subject to any disclaimer, the term of this patent is extended or adjusted under 35 U.S.C. 154(b) by 0 days.

(21) Appl. No.: 13/942,766

(22) Filed: Jul. 16, 2013

(65) Prior Publication Data

US 2013/0303705 A1    Nov. 14, 2013

Related U.S. Application Data

(62) Division of application No. 11/064,191, filed on Feb. 23, 2005, now Pat. No. 8,519,058.

(60) Provisional application No. 60/546,811, filed on Feb. 23, 2004.

(51) Int. Cl.
*C08F 226/00* (2006.01)

(52) U.S. Cl.
USPC .......... 525/328.2; 528/31; 528/274; 528/288; 528/303; 528/310

(58) Field of Classification Search
USPC .......... 524/555; 525/328.2; 528/31, 274, 288, 528/303, 310
See application file for complete search history.

(56) References Cited

FOREIGN PATENT DOCUMENTS

WO    WO 01/85801    * 11/2001

* cited by examiner

*Primary Examiner* — Gregory Listvoyb
(74) *Attorney, Agent, or Firm* — Kevin S. Dobson

(57) ABSTRACT

Novel, crosslinked polymers using biomass derived materials, such as aldaric acids and derivatives, are provided. The polymers can be used as hydrogels and in antimicrobial compositions.

32 Claims, No Drawings

CROSSLINKED POLYMERS CONTAINING BIOMASS DERIVED MATERIALS

This application is a Divisional of U.S. application Ser. No. 11/064,191, now granted, filed on Feb. 23, 2005.

FIELD OF INVENTION

The invention is directed to the preparation of novel, crosslinked polymers using biomass derived materials, such as aldaric acids and derivatives. These polymers can be used as hydrogels.

BACKGROUND

The concept of using biomass-derived materials to produce other useful products has been explored since man first used plant materials and animal fur to make clothing and tools. Biomass derived materials have also been used for centuries as adhesives, solvents, lighting materials, fuels, inks/paints/coatings, colorants, perfumes and medicines. Recently, people have begun to explore the possibility of using "refined biomass" as starting materials for chemical conversions leading to novel high value-in-use products. Over the past two decades, the cost of renewable biomass materials has decreased to a point where many are competitive with those derived from petroleum. In addition, many materials that cannot be produced simply from petroleum feedstocks are potentially available from biomass or refined biomass. Many of these unique, highly functionalized, molecules would be expected to yield products unlike any produced by current chemical processes. "Refined biomass" is purified chemical compounds derived from the first or second round of plant biomass processing. Examples of such materials include cellulose, sucrose, glucose, fructose, sorbitol, erythritol, and various vegetable oils.

A particularly useful class of refined biomass is that of aldaric acids. Aldaric acids, also known as saccharic acids, are diacids derived from naturally occurring sugars. When aldoses are exposed to strong oxidizing agents, such as nitric acid, both the aldehydic carbon atom and the carbon bearing the primary hydroxyl group are oxidized to carboxyl groups. An attractive feature of these aldaric acids includes the use of very inexpensive sugar based feedstocks, which provide low raw material costs and ultimately could provide low polymer costs if the proper oxidation processes are found. Also, the high functional density of these aldaric acids provide unique, high value opportunities, which are completely unattainable at a reasonable cost from petroleum based feedstocks.

Hydrogels (hydrated gel) are polymers that contain water-swellable, three-dimensional networks of macromolecules held together by covalent or noncovalent (e.g., ionic or hydrogen bonded) crosslinks. Upon placement in an aqueous environment, these networks swell to the extent allowed by the degree of crosslinking. They are used in many fields such as medical applications, personal care formulations, coatings, and surfactants.

U.S. Pat. No. 5,496,545 discloses crosslinked polyallylamine and polyethyleneimine. The crosslinking agents disclosed include epichlorohydrin, diepoxides, diisocyanates, α,ω-dihaloalkanes, diacrylates, bisacrylamides, succinyl chloride, and dimethyl succinate. The present invention provides new crosslinked polymers that can function as hydrogels. The polymers comprise crosslinking moieties that can be derived from biomass sources.

SUMMARY OF THE INVENTION

One aspect of the present invention is a crosslinked polymer comprising:

a linear, branched or cyclic polymeric backbone comprising repeat units that comprise one or more of each of: hydrocarbylene groups, heteroatoms, and carbonyl carbon groups; wherein the hydrocarbylene groups are aliphatic or aromatic, linear, branched, or cyclic, and can include combinations of aliphatic, aromatic, linear, branched and/or cyclic hydrocarbylene groups; and one or more crosslinking units containing at least one aldaroyl structural unit of Formula I:

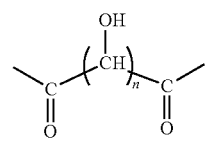

where n is 1-6.

The hydrocarbylene groups and heteroatoms of the repeat units are optionally substituted with substituents that comprise one or more of $C_1$-$C_{30}$ hydrocarbylene groups, heteroatoms, and carbonyl carbon groups, wherein the hydrocarbylene groups of the substituents are aliphatic or aromatic, linear, branched, or cyclic, or combinations thereof.

Preferably the crosslinking units are one or more of Formulae II, III, IV, and V:

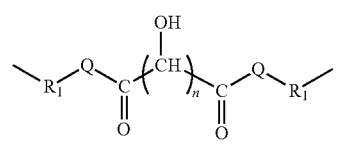

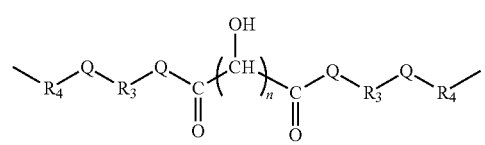

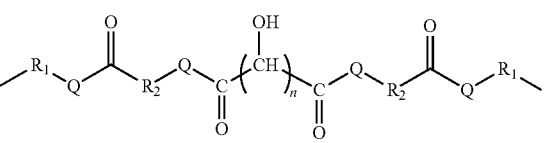

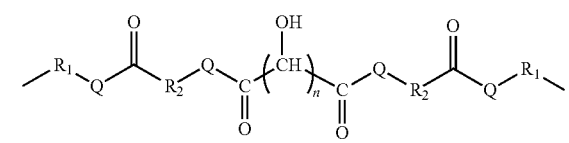

wherein Q is —O— or —NH—, or salts thereof, and $R_1$, $R_2$, $R_3$ and $R_4$ are aliphatic or aromatic hydrocarbylene groups, linear, branched or cyclic, optionally substituted, and optionally containing —O—, —Si(ZZ')O—, —(C=O)— or —NZ— linkages, where Z and Z' are independently hydrogen, alkyl, substituted alkyl, alkaryl, substituted alkaryl, aryl, or substituted aryl;

and wherein Formulae II, III, IV, and V are directly attached to the polymer backbone.

Another aspect of the present invention is a crosslinked polymer prepared by a process comprising contacting a crosslinking agent with a substrate polymer to form a crosslinked polymer, wherein the crosslinking agent is one or more of Formulae VI, VII and VIII:

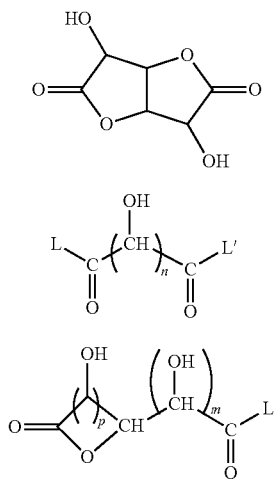

wherein L and L' independently contain a suitable functional group, and n=1-6, m=0-4, and p=1-4;

and the substrate polymer comprises:

a linear, branched or cyclic polymeric backbone comprised of repeat units that comprise one or more of hydrocarbylene groups, heteroatoms, and carbonyl carbon groups wherein the hydrocarbylene groups are aliphatic or aromatic, linear, branched, or cyclic, or combinations thereof; and reactive pendant groups attached to the polymeric backbone, the pendant groups being of the formula -G or —R-G, wherein G is a nucleophile or electrophile;

wherein R is independently linear, cyclic, or branched alkylene, arylene, or alkarylene groups of 1-22 carbon atoms, optionally substituted with alkyl, aryl, hydroxy, amino, carbonyl, ester, amide, alkoxy, nitrile or halogen, and optionally containing —O—, —Si(ZZ')O—, —(C=O)— or —NZ— linkages, where Z and Z' are independently hydrogen, alkyl, substituted alkyl, alkaryl, substituted alkaryl, aryl, or substituted aryl. The hydrocarbylene groups and heteroatoms of the repeat units are optionally substituted with substituents that comprise one or more of $C_1$-$C_{30}$ hydrocarbylene groups, heteroatoms, and carbonyl carbon groups. The hydrocarbylene groups of the substituents can be aliphatic or aromatic, linear, branched, or cyclic, or combinations thereof. Preferably, L and L' are derived from an amine, hydroxyl, carboxylic acid, ester, urethane, urea, amide, or isocyanate; and G is an epoxide, isocyanate, benzylic halide, amine, acid halide, ester, or amide. Also preferably L and L' are selected from optionally substituted —NHR", —OR", and hydrocarbylene-C(=O)OR" and G is selected from —NH$_2$, —C(=O)Cl, —C(=O)OR", or —C(=O)NH—R"—NH$_2$; wherein R" is independently an optionally substituted hydrocarbyl or hydrocarbylene, and wherein n=2-4, m=0-1, and p=2-3. The optional substituents on R" can be any heteroatom-containing group that does not participate directly in reactions between the substrate polymer and the crosslinking agent; i.e., the substituent is preferably not displaced during such reaction and does not form a covalent bond with the substrate polymer. Groups attached to the polymer by reaction with G can contain aza (—NZ—) or ether (—O—) linkages (e.g., G can be PEGylated). In one embodiment of the process, less than 100% of the reactive pendant groups are derivatized such that the derivatized pendant groups are substantially unreactive to the crosslinking agent. "Substantially unreactive", as used herein, means having a rate of reaction, e.g., with the crosslinking agent, of about 20% or less of the rate of reaction of an underivatized pendant group under the same conditions. The derivatization can be performed before, during or after contact of the crosslinking group with the polymer substrate. Preferably, the reactive pendant groups are derivatized to contain an optionally substituted aliphatic carbon chain with optional —(NZ)—, and —O— linkages, where Z is hydrogen, optionally substituted alkyl or optionally substituted aryl.

In another embodiment, the crosslinking agent is derived from an aldaric acid, aldarolactone, aldarodilactone, aldarolactone ester, aldaric acid monoester, aldaric acid diester, or aldaramide, or salts thereof, and the substrate polymer comprises polyallylamine, polyallylamine hydrochloride, branched polyethyleneimine, branched polyethyleneimine hydrochloride, poly(acryloyl chloride), poly(methacryloyl chloride), poly[N-(ω-aminoalkyl)acrylamide], polyglycosamine, carboxymethylchitosan, chitosan, chitosan hydrochloride, or derivatives or salts thereof. By "derived from" is meant that the crosslinking agent can be produced from a starting compound in about six or fewer chemical reaction steps, and retains an aldaric structure —C(=O)(CHOR)$_n$C(=O)— wherein R is H or a carbon-containing group such as alkyl.

Preferably the crosslinking agent is one or more of the Formulae IX, X, XI, and XII:

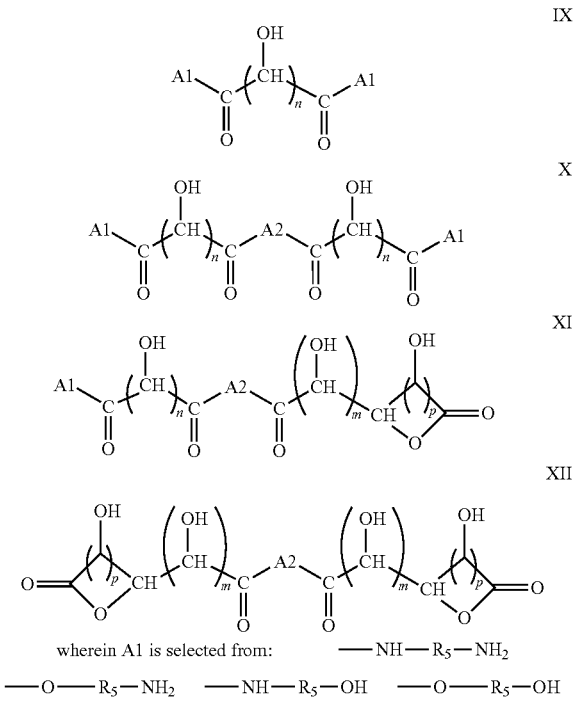

-continued

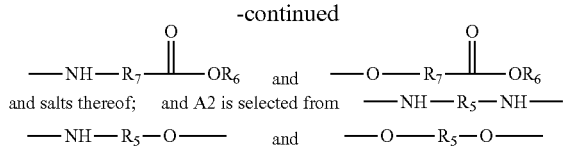

and salts thereof;

wherein $R_5$ and $R_7$ are independently aliphatic or aromatic hydrocarbylene groups, linear, branched or cyclic, optionally substituted, and optionally containing —O—, —Si(ZZ')O—, —(C=O)— or —NZ— linkages, where Z and Z' are independently hydrogen, alkyl, substituted alkyl, alkaryl, substituted alkaryl, aryl, or substituted aryl; and $R_6$ is hydrogen or a 1-22 carbon alkyl group.

The polymers and processes can be used to form compositions, emulsifiers, thickeners, and personal care products comprising the polymers. Examples of personal care products that can be made from the polymers include skin and hair conditioners. In some embodiments, the polymers or products made therefrom are antimicrobial.

Other aspects of the invention include a method of cleaning and smoothing human skin and a method of conditioning hair comprising the application of an effective amount of the polymers of the invention. Also included are methods for killing, inhibiting, or preventing the growth of at least one microbe, the method comprising contacting the microbe with an effective amount of a crosslinked polymer according to the invention, a method of reducing microbial population on a surface comprising contacting a surface with an effective amount of the crosslinked polymer for a time sufficient to reduce the microbial population on the surface, an antimicrobial substrate comprising a crosslinked polymer according to the invention that is bound to or incorporated into the substrate, and articles comprising such antimicrobial substrates.

These and other aspects of the present invention will be apparent to one skilled in the art, in view of the following description and the appended claims.

DETAILED DESCRIPTION

The following definitions may be used for the interpretation of the present specification and the claims:

By hydrocarbyl is meant a straight chain, branched or cyclic arrangement of carbon atoms connected by single, double, or triple carbon-to-carbon bonds, and substituted accordingly with hydrogen atoms. Hydrocarbyl groups can be aliphatic and/or aromatic. Examples of hydrocarbyl groups include methyl, ethyl, propyl, isopropyl, butyl, isobutyl, t-butyl, cyclopropyl, cyclobutyl, cyclopentyl, methylcyclopentyl, cyclohexyl, methylcyclohexyl, benzyl, phenyl, o-toluoyl, m-toluoyl, p-toluoyl, xylyl, vinyl, allyl, butenyl, cyclohexenyl, cyclooctenyl, cyclooctadienyl, and butynyl. Examples of substituted hydrocarbyl groups include toluoyl, chlorobenzyl, —($CH_2$)—O—($CH_2$)—, fluoroethyl, p-($CH_3S$)$C_6H_5$, 2-methoxypropyl, and ($CH_3$)$_3SiCH_2$.

"Alkyl" means a saturated hydrocarbyl group. Examples of alkyl groups include methyl, ethyl, propyl, isopropyl, butyl, s-butyl, isobutyl, pentyl, neopentyl, hexyl, heptyl, isoheptyl, 2-ethylhexyl, cyclohexyl and octyl.

"Aryl" means a group defined as a monovalent radical formed conceptually by removal of a hydrogen atom from a hydrocarbon that is structurally composed entirely of one or more benzene rings. Examples of aryl groups include benzene, biphenyl, terphenyl, naphthalene, phenyl naphthalene, and naphthylbenzene.

"Alkaryl" means an alkylated aryl group; that is, an aryl group as defined above that is substituted with an alkyl group.

By "hydrocarbylene," "alkylene," "arylene," or "alkarylene" is meant the divalent form of the corresponding group.

"Substituted" means that a group contains one or more substituent groups, or "substituents," that do not cause the compound to be unstable or unsuitable for the use or reaction intended. Unless otherwise specified herein, when a group is stated to be "substituted" or "optionally substituted," substituent groups that can be present include carboxyl, carboxamido (including primary, secondary or tertiary carboxamido), acylamino, alkoxycarbonylamino, sulfonylamino, cyano, alkoxy, alkoxycarbonyl, acyloxy, fluoro, chloro, bromo, iodo, amino (including primary, secondary and tertiary amino), hydroxy, alkenyl, oxo, imino, hydroxyimino, hydrocarbyloxyimino, wherein the hydrocarbyl group can be aliphatic, aryl or a combination of the two, trihydrocarbylsilyl, wherein each hydrocarbyl group can be independently alkyl or aryl, trihydrocarbylsiloxy, wherein each hydrocarbyl group can be independently alkyl or aryl, nitro, nitroso, hydrocarbylthio, wherein the hydrocarbyl group can be aliphatic, aryl or a combination of the two, hydrocarbylsulfonyl, wherein the hydrocarbyl group can be aliphatic, aryl or a combination of the two, hydrocarbylsulfinyl, wherein the hydrocarbyl group can be aliphatic, aryl or a combination of the two, hydrocarbyloxysulfonyl, wherein the hydrocarbyl group can be aliphatic, aryl or a combination of the two, sulfonamido (including primary, secondary and tertiary sulfonamido), sulfonyl, dihydrocarbylphosphino, wherein each hydrocarbyl group can be independently alkyl or aryl, dihydrocarbyloxyphosphino, wherein each hydrocarbyl group can be independently alkyl or aryl, hydrocarbylphosphonyl, wherein the hydrocarbyl group can be aliphatic, aryl or a combination of the two, hydrocarbyloxyphosphonyl, wherein the hydrocarbyl group can be aliphatic, aryl or a combination of the two, phosphonamido (including primary, secondary and tertiary phosphonamido), and salts of the aforementioned.

The present invention is directed to a crosslinked polymer comprising a polymeric backbone and one or more crosslinking units containing at least one aldaroyl unit.

The polymer comprises:

A) a linear, branched or cyclic polymeric backbone comprising repeat units that comprise one or more groups selected from hydrocarbylene groups, heteroatoms, and carbonyl carbon groups, wherein the hydrocarbylene groups are aliphatic or aromatic, linear, branched, or cyclic, or combinations thereof; and B) one or more crosslinking units containing at least one aldaroyl structural unit of Formula I:

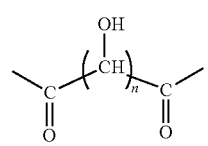

where n is 1-6.

The hydrocarbylene groups and heteroatoms of the repeat units are optionally substituted with substituents that comprise one or more of $C_1$-$C_{30}$ hydrocarbylene groups, heteroatoms, and carbonyl carbon groups, wherein the hydrocarbylene groups of the substituents are aliphatic or aromatic, linear, branched, or cyclic, or combinations thereof.

The crosslinker shown in Formula I is attached to the polymer backbone via the available valences at either end of the structural unit. They are attached either directly with no other atoms between the structure of Formula I and the backbone of the polymer, or indirectly with other atoms or structural groups between Formula I and the polymer backbone. For example, in one embodiment shown below, the crosslinking unit (in which n=4) is indirectly attached to the polyethylene backbone via the —NH—CH$_2$—C(=O)—NH—CH$_2$— structural unit:

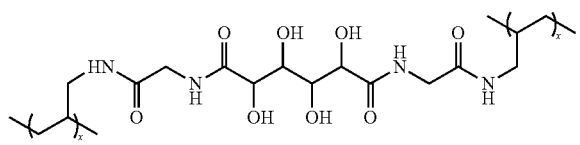

Aldaric acids are diacids derived from naturally occurring sugars. When aldoses are exposed to strong oxidizing agents, such as nitric acid, both the aldehydic carbon atom and the carbon bearing the primary hydroxyl group are oxidized to carboxyl groups. This family of diacids is known as aldaric acids (or saccharic acids). An aldarolactone has one carboxylic acid lactonized; the aldarodilactone has both lactonized. As illustration, the aldaric acid derivatives starting from D-glucose are shown below.

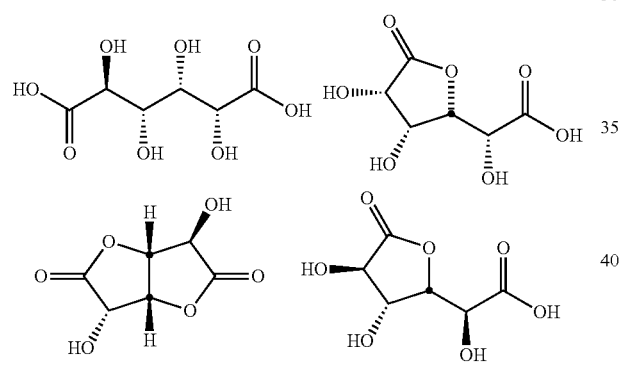

Any stereoisomer or mixture of stereoisomers can be used in the compositions and processes disclosed herein. The aldaric acid derivative can be glucaric acid or galactaric acid, or their derivatives such as, for example, glucarolactone, glucarodilactone, galactarolactone, and dimethyl galactarate.

The polymeric backbone can contain —NZ—, —N$^+$ZZ'—, —O—, —C(=O)NZ—, —C(=O)O—, —C(=O)—, —OC(=O)O—, —OC(=O)NZ—, —NZC(=O)NZ'—, or —SiZZ'O— linkages, where Z and Z' are independently hydrogen, alkyl, substituted alkyl, aryl, or substituted aryl. Substituents on the repeat units contain one or more of —X, —O(Z), —N(ZZ'), —N$^+$(ZZ'Z''), —C(=O)OZ, —C(=O)X, —C(=O)NZZ', —C=N=O, —O—, —N(Z)—, —N$^+$(ZZ)—, —C(=O)N(Z)—, —C(=O)O—, —C(=O)—, —OC(=O)O—, —OC(=O)N(Z)—, —N(Z)C(=O)N(Z')—, —C(=O)NH(CH$_2$)$_p$NH$_2$, —Si(ZZ')O—, —(OCH$_2$CH$_2$)$_m$OH, or —(OSi(ZZ'))$_n$OH, or salts thereof, wherein X is a halogen, Z, Z', and Z'' are independently hydrogen or C$_1$-C$_{22}$ optionally substituted alkyl or aryl, and wherein m is 1 to 50, n is 1 to 100, and p is 1 to 12.

The repeat units of the crosslinked polymer preferably comprise aliphatic hydrocarbylene groups with substituents comprising one or more of aminoalkyl groups, —C(=O)OZ, —C(=O)X, —C(=O)NZZ', or —C(=O)NH(CH$_2$)$_p$NH$_2$, or salts thereof. The repeat units are also preferably azahydrocarbylenes or salts thereof, with one or more terminal aminoalkyl groups or salts thereof as substituents on the nitrogen of the azahydrocarbylene repeat unit. Also preferably the repeat units contain substituents comprising one or more of C$_1$-C$_{22}$ aminoalkyl groups, optionally substituted with alkyl or aldaroyl groups or salts thereof. The aldaroyl moiety in the crosslinking unit is preferably glucaroyl, galactaroyl, mannaroyl, xylaroyl, or tartaroyl.

In one embodiment, the crosslinked polymer is a derivative of polyallylamine, polyallylamine hydrochloride, branched polyethyleneimine, branched polyethyleneimine hydrochloride, poly(acryloyl chloride), poly(methacryloyl chloride), poly[N-(ω-aminoalkyl)acrylamide], polyglycosamine, carboxymethylchitosan, chitosan, chitosan hydrochloride, or a derivative or salt thereof. For example, polymers having amine groups can have some of the amine groups alkylated, acylated, sulfonated, or reacted to form imines or aminals. Also, they can be in one or more salt forms or partial salt forms, e.g., polyallyamine hydrochloride can be converted to its p-toluenesulfonic acid or acetic acid salt. Polymers with acyl chloride groups can be partially reacted with a monofunctional alcohol or amine to form ester or amide side chains. Such derivatives retain the backbone structure and preferably some of the reactive side chain structure as the original polymer from which the derivative is derived. The crosslinked polymer can additionally comprise one or more of the crosslinking units of Formulae II, III, IV, or V:

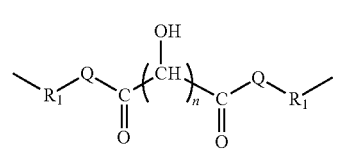

II

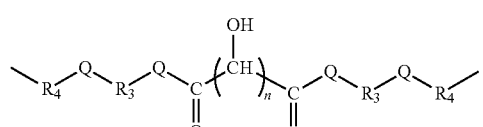

III

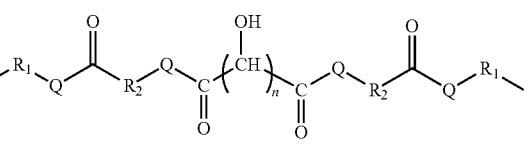

IV

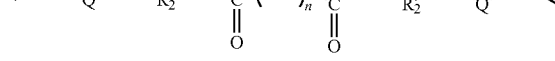

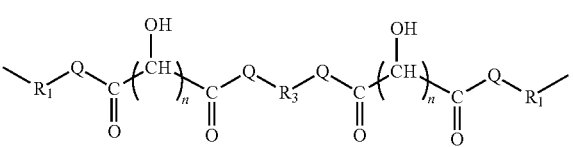

V wherein Q is —O— or —NH—, or a salt thereof, and R$_1$, R$_2$, R$_3$ and R$_4$ are aliphatic or aromatic hydrocarbylene groups, linear, branched or cyclic, optionally substituted, and optionally containing —O—, —Si(ZZ')O—, —(C=O)— or —NZ— linkages, where Z and Z' are independently hydrogen, alkyl, substituted alkyl, alkaryl, substituted alkaryl, aryl, or substituted aryl.

The crosslinking units shown by Formulae III, IV, and V are directly attached to the polymer backbone via the available valences at either end of the structural units.

Preferably, $R_1$ is —[(CH$_2$)$_{0-22}$]—, —(CH$_2$)$_a$C$_6$H$_{10}$(CH$_2$)$_b$—, —(CH$_2$CH$_2$NH)$_{1-22}$CH$_2$CH$_2$—, —[(CH$_2$CH(Z')O)$_{1-22}$(CH$_2$)$_{2-3}$]— wherein Z' is H or CH$_3$, —C(O)NH(CH$_2$)$_{2-22}$—, or —(CH$_2$)$_a$(C$_6$H$_4$)(CH$_2$)$_b$—, wherein a=0-6 and b=0-6;

$R_2$ is —[(CH$_2$)$_{1-21}$]—, —CH(CH$_3$)—, —CH(isopropyl)-, —CH(isobutyl)-, —CH(CH(CH$_3$)CH$_2$CH$_3$)—, —CH(CH$_2$OH)—, —CH(CH$_2$CH$_2$SCH$_3$)—, —C(CH(CH(OH)CH$_3$)—, —CH(CH$_2$C$_6$H$_5$)—, —CH(CH$_2$C$_6$H$_4$H)—, —CH(CH$_2$CONH$_2$)—, or —CH(CH$_2$CH$_2$CONH$_2$)—;

$R_3$ is —[(CH$_2$)$_{2-22}$]—, —[(CH$_2$)$_{0-6}$(C$_6$H$_{10}$)(CH$_2$)$_{0-6}$]—, —[(CH$_2$)$_{0-6}$C$_6$H$_4$(CH$_2$)$_{0-6}$]—, —[CH$_2$CH$_2$(OCH$_2$CH$_2$)$_{1-21}$]—, —[CH$_2$CH(CH$_3$)[OCH$_2$CH(CH$_3$)]$_{1-21}$]—, —(CH$_2$CH$_2$NH)$_{1-22}$CH$_2$CH$_2$—, —[CH$_2$CH(CH$_3$)[OCH$_2$CH(CH$_3$)]$_x$(OCH$_2$CH$_2$)$_y$[OCH$_2$CH(CH$_3$)]$_z$]— wherein x+y+z=2-50, —[CH$_2$CH$_2$(OCH$_2$CH$_2$)$_x$[OCH$_2$CH(CH$_3$)]$_y$(OCH$_2$CH(CH$_3$))$_y$(OCH$_2$CH$_2$)$_z$]— wherein x+y+z=2-50, —[CH(CH$_3$)CH$_2$O]$_x$CH$_2$C(Z')(CH$_2$[OCH$_2$CH(CH)]$_y$—)CH$_2$[OCH$_2$CH(CH$_3$)]$_z$— wherein x+y+z=2-10 and Z' is H, methyl or ethyl, —[CH(CH$_3$)CH$_2$O]$_x$CH$_2$CH([OCH$_2$CH(CH$_3$)]$_y$—)CH$_2$[OCH$_2$CH(CH$_3$)]$_z$— wherein x+y+z=3-100, or —CH$_2$CH$_2$CH$_2$[CH(NH$_2$)CONHCH$_2$CH$_2$CH$_2$]$_{0-10}$CH(COYR)— or salts thereof, wherein Y is O or NH, and R is a C$_1$-C$_{22}$ optionally substituted alkyl, aryl, or alkaryl; and $R_4$ is —C(=O)—, —C$_6$H$_4$CH$_2$—, —(CH$_2$)$_{1-22}$Y'CH$_2$CH(OH)CH$_2$—, or —(CH$_2$)$_{1-22}$Y'C(O)CH(OH)CH$_2$—, wherein Y is O or NH.

The $R_3$ moieties, —[H(CH$_3$)CH$_2$O]$_x$CH$_2$C(Z')CH$_2$[OCH$_2$CH(CH$_3$)]$_y$—)CH$_2$[OCH$_2$CH(CH$_3$)]$_z$— and —[CH(CH$_3$)CH$_2$O]$_x$CH$_2$CH([OCH$_2$CH(CH$_3$)]y)CH$_2$[OCH$_2$CH(CH$_3$)$_z$]—, are trivalent and therefore can react to form crosslinked structures. Other polyalkylene, polyalkyleneoxide, and polyalkylenearyl structures can be trivalent, tetravalent, or higher multivalent. Therefore, when $R_3$ is multivalent, the polymer of the instant invention can exist in a multivalent crosslinked structure with the empty valences on the polyalkyleneoxide being endcapped by available functionalities such as amines.

Preferably about 0.1% to about 100% of the polymer backbone repeat units are connected to a crosslinking unit. More preferably about 1% to about 30% of the polymer backbone repeat units are connected to a crosslinking unit.

Also provided according to the invention are crosslinked polymers prepared by a process comprising contacting a crosslinking agent with a substrate polymer to form a crosslinked polymer, wherein the crosslinking agent is one or more of Formulae VI, VII and VIII:

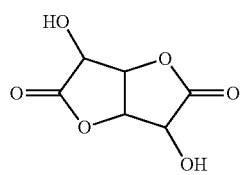

VI

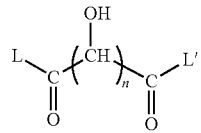

VII

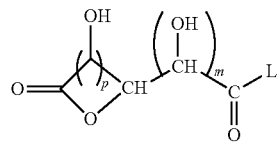

VIII and n=1-6, m=0-4, and p=1-4. Preferably n=2-4, m=0-1, and p=2-3.

The substrate polymer used in the instant process comprises a linear, branched or cyclic polymeric backbone. The backbone contains repeat units that comprise one or more of hydrocarbylene groups, heteroatoms, and carbonyl carbon groups. The hydrocarbylene groups are aliphatic or aromatic, linear, branched, or cyclic, or combinations thereof. The hydrocarbylene groups and heteroatoms of the repeat units are optionally substituted with substituents that comprise one or more of C$_1$-C$_{30}$ hydrocarbylene groups, heteroatoms, and carbonyl carbon groups, wherein the hydrocarbylene groups of the substituents are aliphatic or aromatic, linear, branched, or cyclic, or combinations thereof.

The polymeric backbone used in the process can contain —NZ—, —N$^+$ZZ'—, —O—, —C(=O)NZ—, —C(=O)O—, —C(=O)—, —OC(=O)O—, —OC(=O)NZ—, —NZC(=O)NZ'—, or —SiZZ'O— linkages, where Z and Z' are independently hydrogen, alkyl, substituted alkyl, aryl, or substituted aryl.

The substituents on the repeat units are preferably one or more of —X, —O(Z), —N(ZZ'), —N$^+$(ZZ'Z''), —C(=O)OZ, —C(=O)X, —C(=O)NZZ', —C=N—O, —O—, —N(Z)—, —N$^+$(ZZ')—, —C(=O)N(Z)—, —C(=O)O—, —C(=O)—, —OC(=O)O—, —OC(=O)N(Z)—, —N(Z)C(=O)N(Z')—, —C(=O)NH(CH$_2$)$_p$NH$_2$, —Si(ZZ')O—, —(OCH$_2$CH$_2$)$_m$OH, or —(OSi(ZZ'))$_n$OH, or salts thereof, where X is a halogen, Z, Z', and Z'' are independently hydrogen, C$_1$-C$_{22}$ optionally substituted alkyl, or C$_1$-C$_{22}$ optionally substituted aryl, and where m is 1 to 50, n is 1 to 100, and p is 1 to 12. More preferably, the substituents comprise one or more of C$_1$-C$_{22}$ aminoalkyl groups, optionally substituted with alkyl or aldaroyl, or a salt thereof. The repeat units preferably comprise aliphatic hydrocarbylene groups with substituents comprising one or more of aminoalkyl groups, —C(=O)OZ, —C(=O)X, —C(=O)NZZ', or —C(=O)NH(CH$_2$)$_n$NH$_2$, or salts thereof, where X is halogen, Z and Z' are independently hydrogen, C$_1$-C$_{22}$ alkyl, substituted alkyl, aryl, or substituted aryl, and n=1-12.

The repeat unit can be an azahydrocarbylene or salt thereof with one or more terminal amino groups or salts thereof as substituents on the N of the azahydrocarbylene repeat unit.

The substrate polymer can also comprise polyallylamine, polyallylamine hydrochloride, branched polyethyleneimine, branched polyethyleneimine hydrochloride, poly(acryloyl chloride), poly(methacryloyl chloride), poly[N-(ω-aminoalkyl)acrylamide], polyglycosamine, carboxymethylchitosan, chitosan, chitosan hydrochloride, or derivatives or salts thereof.

Attached to the polymeric backbone are reactive pendant groups of the formula -G or —R-G; where G is a nucleophile or electrophile; and where R is independently linear, cyclic, or branched alkylene, arylene, or alkarylene groups of 1-22 carbon atoms, optionally substituted with alkyl, aryl, hydroxy, amino, carbonyl, ester, amide, alkoxy, nitrile or halogen, and optionally containing —O—, —Si(ZZ')O—, —(C=O)— or —NZ— linkages, where Z and Z' are independently hydrogen, alkyl, substituted alkyl, alkaryl, substituted alkaryl, aryl, or substituted aryl.

The terms, "electrophile" and "nucleophile," are well known to those skilled in the art, and can be broadly defined as reactive chemical moieties that act as electron acceptors or electron donors respectively. Preferably, G is an epoxide, isocyanate, benzylic halide, amine, acid halide, ester, or amide; more preferably G is —$NH_2$, —C(=O)Cl, —C(=O)OR" or —C(=O)NH—R"—$NH_2$ wherein R" is independently hydrogen or an optionally substituted hydrocarbyl or hydrocarbylene. Most preferably G is —$NH_2$.

L and L' are defined as containing a suitable functional group. A suitable functional group is herein defined as a functional group that readily forms a covalent bond with the reactive pendant group. The functional group employed depends upon the synthetic method used to make the crosslinked polymer. The functional group can contain heteroatoms such as O, N, S, and/or can be derived from a functional group such as an amine, hydroxyl, carboxylic acid, ester, urethane, urea, amide, or isocyanate. Particularly useful functional groups are those that contain a —NH— group, a —C(=O)O— group, a —O— group, or salts thereof. Preferably, the suitable functional group is derived from an amine, hydroxyl, carboxylic acid, ester, urethane, urea, amide, or isocyanate. More preferably L and L' are independently selected from —Y—R, wherein Y is O, NH, or S and R is alkyl, substituted alkyl, alkaryl, substituted alkaryl, aryl, or substituted aryl. Also more preferably L and L' are independently selected from optionally substituted —NHR", —OR", and hydrocarbylene-C(=O)OR"; wherein R" is an optionally substituted hydrocarbylene, and wherein n=2-4, m=0-1, and p=2-3.

As illustration, a crosslinker that is capped with a carboxylic acid as the suitable functional group would be expected to react readily with available amine pendant groups on the polymeric backbone. A crosslinker end-capped with a hydroxyl group or an amine as a functional group would not be expected to react with the pendant amine functionality of the polymeric backbone. However, if the subject polymer backbone had a carboxylic acid or an isocyanate as pendant functionality, then a crosslinker capped with an amine or a hydroxyl functional group could react with the pendant group of the polymeric backbone.

In another embodiment, less than 100%, preferably up to about 50%, and more preferably up to about 20% of the reactive pendant groups are derivatized so that they are unreactive to the crosslinking agent. The derivatization can be performed by contacting the reactive pendant groups with a derivatizing reagent before, during or after contact of the crosslinker with the substrate polymer. Preferably, the reactive pendant groups are derivatized before the contact of the crosslinker with the polymer substrate. The reactive pendant groups can be derivatized to contain an optionally substituted aliphatic carbon chain with optional —(NZ)—, and —O— linkages, where Z is hydrogen, optionally substituted alkyl or optionally substituted aryl. Preferably, the reactive pendant groups are derivatized to contain a linear or branched alkyl group of 1-22 carbon atoms, optionally substituted with —O— linkages, and optionally substituted with —$NH_2$, halogen, hydroxyl, or carbonyl groups, or salts thereof, more preferably a $C_1$-$C_{22}$ alkyl group, most preferably a $C_2$-$C_{18}$ unsubstituted alkyl group.

The crosslinking agent can be derived from an aldaric acid, aldarolactone, aldarodilactone, aldarolactone ester, aldaric acid monoester, aldaric acid diester, or aldaramides, or salts thereof. Preferably the crosslinking agent is derived from glucaric acid, galactaric acid, mannaric acid, xylaric acid or tartaric acid.

In another embodiment, the crosslinking agent is of the Formulae IX, X, XI, XII:

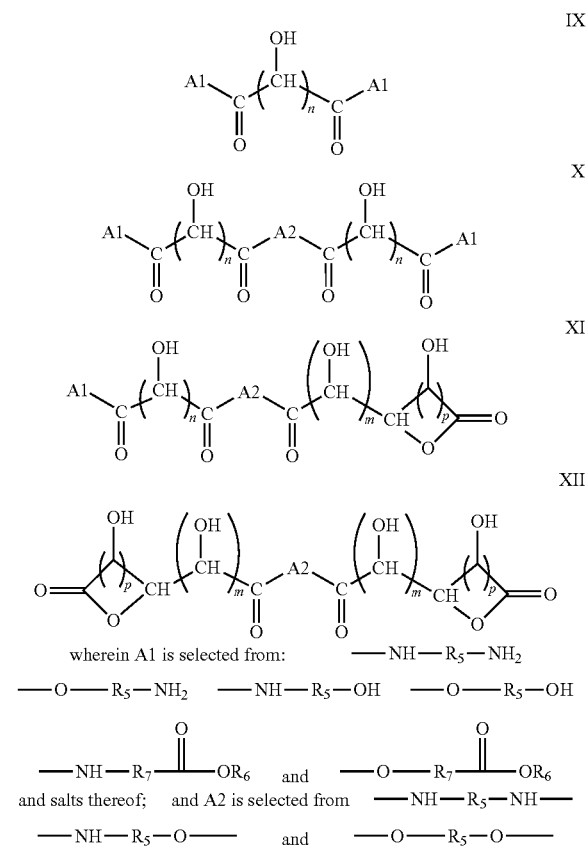

and salts thereof. $R_5$ and $R_7$ are independently aliphatic or aromatic hydrocarbylene groups, linear, branched or cyclic, optionally substituted with alkyl, aryl, hydroxy, amino, carbonyl, carboxyl, ester, amide, alkoxy, nitrile or halogen, or slats thereof, and optionally containing —O—, —Si(ZZ')O—, —(C=O)— or —NZ— linkages, where Z and Z' are independently hydrogen, alkyl, substituted alkyl, alkaryl, substituted alkaryl, aryl, or substituted aryl; and $R_6$ is hydrogen or a 1-22 carbon alkyl group.

Preferably, $R_5$ and $R_7$ are independently optionally substituted aliphatic carbon chains with optional —(NZ)— or —O— linkages, wherein Z is hydrogen, optionally substituted alkyl or optionally substituted aryl. More preferably, $R_5$ and $R_7$ are independently linear, cyclic, or branched alkylene groups of 1-10 carbon atoms, optionally substituted with —O-linkages, and optionally substituted with —$NH_2$ groups, or salts thereof.

Also preferably, $R_7$ is —[$(CH_2)_{1-21}$]—, —$CH(CH_3)$—, —CH(isopropyl)-, —CH(isobutyl)-, —$CH(CH(CH_3)CH_2CH_3)$—, —$CH(CH_2OH)$—, —$CH(CH_2CH_2SCH_3)$—, —$CH(CH(OH)CH_3)$—, —$CH(CH_2C_6H_5)$—, —$CH(CH_2C_6H_4OH)$—, —$CH(CH_2CONH_2)$—, or —$CH(CH_2CH_2CONH_2)$—; and $R_5$ is —[$(CH_2)_{2-22}$]—, —[$(CH_2)_{0-6}(C_6H_{10})(CH_2)_{0-6}$]—, —[$(CH_2)_{0-6}C_6H_4(CH_2)_{0-6}$]—, —[$CH_2CH_2(OCH_2CH_2)_{1-21}$]—, —[$CH_2CH(CH_3)[OCH_2CH(CH_3)]_{1-21}$]—, —(CH$_2$CH$_2$NH)$_{1-22}$CH$_2$CH$_2$—, —[CH$_2$CH(CH$_3$)[OCH$_2$CH(CH$_3$)]$_x$(OCH$_2$CH$_2$)$_y$[OCH$_2$CH(CH$_3$)]$_z$]— wherein x+y+z=2-50, —[CH$_2$CH$_2$(OCH$_2$CH$_2$)$_x$[OCH$_2$CH(CH$_3$)]$_y$(OCH$_2$CH$_2$)$_z$]— wherein x+y+z=2-50, —[CH(CH$_3$)CH$_2$O]$_x$CH$_2$C(Z')(CH$_2$[OCH$_2$CH(CH)]$_y$—)CH$_2$[OCH$_2$CH(CH$_3$)]$_z$— wherein x+y+z=2-10 and Z' is H, methyl or ethyl, —[CH(CH$_3$)CH$_2$O]$_x$CH$_2$CH([OCH$_2$CH(CH$_3$)]$_y$—)CH$_2$[OCH$_2$CH(CH$_3$)]$_z$— wherein x+y+z=3-100, or —CH$_2$CH$_2$CH$_2$CH$_2$[CH(NH$_2$)CONHCH$_2$CH$_2$CH$_2$CH$_2$]$_{0-10}$CH(COYR)— or salts thereof, wherein Y is O or NH, and R is a C$_1$-C$_{22}$ optionally substituted alkyl, aryl, or alkaryl.

Examples of polyoxaalkyleneamines that can be used include to those based on Jeffamine® polyether amines (Huntsman LLC, Salt Lake City, Utah). Examples of polytetramethylene glycols that can be used include those based on Terethane® polytetramethyleneetherglycol (E.I. DuPont de Nemours, Wilmington, Del.).

In some embodiments, about 0.0005 to about 0.5 molar equivalents of crosslinking agent per reactive pendant group can be used in the process. Preferably, from about 0.005 to about 0.5 molar equivalents of crosslinking agent are used per reactive pendant group, and more preferably about 0.01 to 0.25 molar equivalents per reactive pendant group.

The processes can be run at any suitable temperature but preferably at about 20° C. to about 100° C. The processes can be carried out in a polymer melt, but are preferably carried out in the presence of a solvent. The choice of solvent is not critical provided the solvent is not detrimental to reactant or product. Preferred solvents include water, dimethylformamide, dimethylformamide LiCl, dimethylacetamide, dimethylacetamide LiCl, ethanol, and methanol.

The polymers disclosed herein are suitable for use as hydrogels. Hydrogels (hydrated gels) are herein defined as materials that absorb large quantities of liquid, i.e., greater than 2 mass equivalents of liquid. They are usually water-swellable, three-dimensional networks of macromolecules held together by covalent or noncovalent crosslinks. When placed in aqueous solution, the networks swell to the extent allowed by the degree of crosslinking.

Hydrogels are useful in many applications, such as medical products, personal care formulations, exfoliants, humectants, surfactants, thickeners, anti-irritants, antimicrobials, lubricants, emulsifiers, delivery agents, coatings, and surfactants. In some embodiments the hydrogels are conducting. The polymers can be modified to introduce a wide range of properties to make them more suitable in such applications. Additionally, divalent crosslinking agents as disclosed herein can be used as water-soluble chain extenders for polyurethanes, and hydroxylated block or comb copolymers made with the processes described herein can be used as pigment dispersants. When used as co-polymers or modifiers to other polymeric materials, the polymers can impart moisture wicking improvements, dyeability, and/or flame resistance to the other materials.

As used herein, the term "antimicrobial" means killing, or preventing or inhibiting the growth of, microorganisms, including bacteria and fungi. "Growth inhibition" means reduced rate of growth of a population of microorganisms. "Growth prevention" means that growth is stopped.

Polymers described herein are also suitable for use in cosmetic products.

Also provided are methods for cleaning and/or smoothing human skin comprising the application of an effective amount of the polymers described herein, and methods of conditioning hair comprising the application of an effective amount of the polymers described herein.

As used herein, "cosmetic products" are products intended for increasing the appeal, visually and/or olfactorily, of the human body. Likewise, "personal care products" are products intended for cleaning, smoothing or other wise improving the health, feel, or well-being of the outside of the human body. These definitions of cosmetic and personal care products at least partially overlap since many products provide functions in both categories. Examples of cosmetic products are: perfumes and like products known as "eau de toilette" and "eau de parfum," hand and body lotions, skin tonics, shaving products, bath and shower products, deodorant and antiperspirant products, hair care products such as shampoos and hair conditioners, and mouth and dental care products. Such products are well known in the art. Thus, examples of skin care products are described in "Harry's Cosmeticology," R. G. Harry, 6$^{th}$ edition, Leonard Hill Books (1973), Chapters 5-13, 18 and 35; examples of deodorants and antiperspirants are described in C. Fox, cosmetics and Toiletries 100 (December 1985), pp 27-41; examples of hair care products are described "Harry's Cosmeticololgy," vide supra, chapters 25-27; examples of dental care products are described in M. Pader, Oral Hygiene: Products and Practice, Marcel Dekker, New York (1988).

For use in the personal care field, the polymers can be modified to enhance moisture retention, lubricity, static control, curl retention, sheen, and/or "body" in hair-care related products. For skin care products could the polymers can be used to make exfoliants (for example, as α-hydroxy acid replacements), humectants, surfactants, thickeners, anti-irritants, antimicrobials, lubricants, emulsifiers, and delivery agents. The polymers can be used to make topical antimicrobial substances or barriers, or as additives to inhibit microbial growth in a separate formulation, or may impart residual antimicrobial activity. Such residual antimicrobial activity can be imparted to a surface, for example, by depositing the polymer onto the surface or by covalently or otherwise attaching the polymer to the surface. Examples of surfaces to which the polymers can be applied include steel, and plastic, although substantially any surface can be treated by application of the polymers. Antimicrobial products containing the polymers can be applied to animal skin, including human skin.

Skin conditioning agents as herein defined include astringents, which tighten skin; exfoliants, which remove exterior skin cells; emollients, which help maintain a smooth, soft, pliable feel and appearance; humectants, which increase the water content of the top layer of skin; occlusives, which retard evaporation of water from the skin's surface; and miscellaneous compounds that enhance the feel and/or appearance of dry or damaged skin or reduce flaking and restore suppleness. Skin conditioning agents are well known in the art, and are disclosed, for example, in Green et al. WO 0107009, and are available commercially from various sources. Examples of skin conditioning agents include alpha-hydroxy acids, beta-hydroxy acids, polyols, hyaluronic acid, D,L-panthenol, polysalicylates, vitamin A palmitate, vitamin E acetate, glycerin, sorbitol, silicones, silicone derivatives, lanolin, natural oils, and triglyceride esters.

The skin care, hair care, and hair coloring compositions made from the polymers can also contain one or more conventional cosmetic or dermatological additives or adjuvants, such as, for example, fillers, surfactants, thixotropic agents, antioxidants, preserving agents, dyes, pigments, fragrances, thickeners, vitamins, hormones, moisturizers, UV absorbing sunscreens, wetting agents, cationic, anionic, nonionic or amphoteric polymers, and hair coloring active substances. Such adjuvants are well known in the field of cosmetics and are disclosed, for example, in "Harry's Cosmeticology," 8$^{th}$ edition, Martin Rieger, ed., Chemical Publishing, New York (2000).

The polymers can also function as surface disinfectants, or as ingredients in a formulation designed to function as a surface disinfectant.

For use in medical applications, the polymers can act as coatings that retain moisture, lubricate, conduct electricity, facilitate sustained release of therapeutic agents, absorb undesirable materials that accumulate in the area of an implant, or act as local antimicrobial agents. The materials of the current invention can be used as components of polymeric medical adhesives (or anti-adhesives), as monomeric crosslinkers, and as components of adhesives that can be deactivated to prevent bandages from creating or enlarging sores on chronically bandaged areas. In the area of medical devices, the polymers can be used as biocompatible agents to attach antimicrobial, anti-inflammatory, or anti-proliferative agents to the surface of catheters, stents, or other medical implants. Sustained release can be accomplished by slow diffusion of at least one biologically active agent out of the polymeric hydrogel matrix. Sustained release can further be facilitated by slow hydrolysis of the crosslink bonds.

In agriculture, uses for the polymers include use as seed coatings, microencapsulating agents (for lower toxicity, slow release, and/or chemical stability), surface tension modifying agents (to improve spreadability or wash-off resistance), or to improve water solubility of non-soluble active ingredients.

EXAMPLES

Unless otherwise stated, in the Examples, the abbreviations used have the following meanings:

| Abbreviation | Ingredient Name |
|---|---|
| 1BrC16 | 1-bromohexadecane |
| 4,9-DODDA | 4,9-dioxa-1,12-dodecanediamine |
| 9DA | 1,9-diaminononane |
| DMG | dimethyl galactarate |
| GA | D-glucaric acid |
| GDL | D-glucaro-1,4:6,3-dilact one |
| HMDA | 1, 6-hexanediamine |
| JEFF | Jeffamine ® |
| JEFF EDR-148 | Jeffamine ® ($H_2NCH_2CH_2OCH_2CH_2OCH_2CH_2NH_2$) |
| JEFF EDR-192 | Jeffamine ® ($H_2NCH_2CH_2(OCH_2CH_2)_3NH_2$) |
| JEFF T5000 | Jeffamine ® polyethertriamine |
| JEFF T403 | Jeffamine ® polypropyleneoxytriamine |
| PAlAmHCl | polyallylamine HCl (obtained from Polysciences, Inc., Warrington, PA) |

Analyses

Unless otherwise specified, the analyses were performed as follows.

Inherent Viscosity ($\eta_{inh}$)

Inherent viscosities were generally run as 0.5% solutions in either hexafluoroisopropanol (HFIP) or m-cresol at 30° C.

Differential Scanning Calorimetry (DSC) and Thermogravimetric Analysis (TGA)

DSC and TGA studies of all polymers were conducted on 5-10 mg samples run at 10° C./min under nitrogen. Sample temperatures spanned ranges beginning as low as −100° C. to as high as 300° C., depending on polymer character and stability. Samples were generally cooled after the first heat cycle and a second heat cycle was then conducted. Generally, polymer DSC results reported are second heat results to eliminate artifacts of thermal history variations.

Swell Factor

Into a pre-dried, tared, 150 mL coarse fritted filter funnel was added about 1 g of polymer. The stem of the funnel was sealed with a rubber stopper. The funnel was placed on a filter flask and about 100 mL of distilled water at about 22° C. is added to the funnel. The contents were stirred, if necessary, to fully disperse the water and polymer. The contents were then left undisturbed for 15 minutes. The rubber stopper was then removed from the stem of the funnel, and suction was applied to the funnel for 5 minutes. The stem and underside of the funnel were then rinsed with ethanol to remove any remaining water droplets and suction was then continued for an additional 5 minutes. Any remaining water droplets were wiped off the funnel with a paper towel. The funnel and contents were then weighed to determine the weight of water retained by the polymer.

Swell factor=(total wt. of wet polymer+funnel)−(total wt. of dry polymer+funnel)

$$\text{wt. of dry polymer} = \frac{(\text{wet wt.} - \text{dry wt.})}{\text{dry wt.}}$$

$$= \frac{\text{g water retained}}{\text{g polymer}}$$

Solubility

Solubilities were generally determined using 0.01 g of test material in 10 mL of test solvent. The vials containing the samples were constantly agitated via a shaker tray at room temperature for anywhere between 24 hours and 4 weeks. Solubility was determined by visual inspection to determine sample homogeneity. Any variance in density gradient, or refractive index was taken as indicating insolubility. Samples deemed to be insoluble were shaken at room temperature for at least 1 week, and in many cases were shaken for 2 weeks or more. A wide range of common solvent types was generally used to allow a broad range of polarity and solvent parameters to come into play.

Film Properties

Film properties were determined on 0.25 inch×2 inch samples cut from larger films spread onto glass with a blade applicator. Generally, films had thicknesses of 5 mil or less. Film properties reported represent an average of at least five measurements for each sample.

The reactions depicted in the following Examples are meant to be illustrative only and not representative of exact structures.

Examples 1-28

Polymers were prepared by first dissolving polyallylamine hydrochloride of ~60,000 molecular weight in water. To that solution was added enough sodium hydroxide to just neutralize the equivalent amount of ammonium hydrochloride functions as would be used by the added GDL. To the partially neutralized polyallylamine hydrochloride was added a water solution of GDL at room temperature. The reaction was substantially over in a matter of minutes. A representative polymerization with GDL is shown below.

The crosslinking was performed using various compounds as described below in a representative reaction with GDL. When another compound was used in the in the crosslinking reaction along with the GDL, such as 9DA, they were both added simultaneously. Into a 250-mL 3-necked round bottom flask equipped with a heating mantle, reflux condenser, nitrogen inlet, and overhead stirrer was added 20 mL of water, 2.80 g (0.030 equivalent, 60,000 MW) of polyallylamine HCl, and 0.26 g (0.0066 mol) of sodium hydroxide. This mixture was stirred at room temperature until a homogeneous solution was achieved (~10 minutes). At this point, a homogeneous solution prepared from 10 mL of water and 0.57 g (0.0033 mol) of GDL was slowly poured at room temperature into the solution containing the polyallylamine HCl. Within 1 to 2 minutes, gel had formed. The gel was then allowed to stir for ~2 hours at room temperature, after which time it was removed from the flask. The gel was then washed 3 times with 100 mL aliquots of methanol followed by THF. The gel was then dried in a vacuum oven at 80° C. to yield 2.79 g (89.1%) of a granular white hydrogel polymer. The results are shown in Table 1. The % crosslinking shown in Table 1 is a theoretical calculation of the % of total amine nitrogens (from the polyallylamine hydrochloride) tied up in the crosslinking process with the aldaric acid. The calculation was based on the total weight of polyallylamine hydrochloride used (molar equivalents of allylamine) and the total molar equivalents of the GDL added to the process. Total final crosslinking was not measured but is assumed since the polymer gelled and became insoluble, although NMR indicated that conversion was less than 100%.

When only 5-15% of the ammonium groups were allowed to react with GDL, a very viscous water solution resulted that could be cast into a film. The resulting films were brittle, but less so than the starting polyallylamine hydrochloride homopolymer. As more ammonium groups reacted with GDL, gels eventually formed. Highly swellable hydrogels (with swell ratios as high as 90) were readily formed when ~22% of the ammonium hydrochloride equivalents were neutralized and GDL was added in an equivalent amount (~11% since both ends of the molecule are assumed to react). The gels were optically clear and colorless.

The data in Tables 1 and 2 show some of the properties that can be obtained in the polymers by varying the ingredients used in making them.

TABLE 1

| Ex. | Composition | Catalyst | Solvent/Media | Color | % Yield | Inh Visc | Inh Sol. | Polym. Character | Swell |
|---|---|---|---|---|---|---|---|---|---|
| 1 | PAlAmHCl/GDL (10:1)-20% crosslinking | triethylamine | water | white | — | insol | HFIP | Powder | 4.72 |
| 2 | PAlAmHCl/GDL (8:1)-25% crosslinking | triethylamine | water | white | — | insol | HFIP | powder-very brittle film | 12.27 |
| 3 | PAlAmHCl/GDL (8.7:1)-23% crosslinking | triethylamine | water | white | — | insol | HFIP | powder-poor film | 80.73 |
| 4 | PAlAmHCl/GDL (5:1)-40% crosslinking | triethylamine | water | off white | 90.1 | insol | HFIP | Powder | 48 |
| 5 | PAlAmHCl/GDL (9.1:1)-22% crosslinking | triethylamine | water | white | — | insol | HFIP | powder-very brittle film | 28.1 |
| 6 | PAlAmHCl/GDL (9.1:1)-22% crosslinking | sodium hydroxide | water | white | 89.1 | insol | HFIP | Powder | 89.5 |
| 7 | PAlAmHCl/GDL (9.1:1)-22% crosslinking | calcium hydroxide | water | white | 84.7 | insol | HFIP | Powder | 88.5 |
| 8 | PAlAmHCl/GDL (9.1:1)-22% crosslinking | calcium hydroxide | water | white | — | insol | HFIP | powder-poor film, very brittle | 6.36 |
| 9 | PAlAmHCl/GDL (9.1:1)-22% crosslinking | calcium hydroxide | water | white | — | insol | HFIP | powder-poor film, very brittle | sol. in water |
| 10 | PAlAmHCl/(GDL/JEFF EDR-148 (2:1))-20% crosslinking | sodium hydroxide | water | white | 68.1 | insol | water | powder-brittle, clear film | 71.3 |
| 11 | PAlAmHCl/(GDL/JEFF EDR-192 (2:1))-20% crosslinking | sodium hydroxide | water | white | 92.9 | insol | water | powder-brittle, clear film | 49 |
| 12 | PAlAmHCl/(GDL/JEFF T5000 (3:1))-10% crosslinking | sodium hydroxide | water/ethanol | white | 40 | insol | water | Powder | 40.1 |
| 13 | PAlAmHCl/(GDL/JEFF T5000 (3:1))-20% crosslinking | sodium hydroxide | water/ethanol | white | 31.9 | insol | water | Powder | 8.04 |
| 14 | PAlAmHCl/(GDL/JEFF T5000 (3:1))-5% crosslinking | sodium hydroxide | water/ethanol | white | 28.4 | insol | water | powder-poor film | sol. in water |
| 15 | PAlAmHCl/(GDL/JEFF T5000 (3:1))-1% crosslinking | sodium hydroxide | water/ethanol | white | — | insol | water | powder-poor, clear, brittle film | sol. in water |
| 16 | PAlAmHCl/(GDL/JEFF T5000 (3:1))-3% crosslinking | sodium hydroxide | water/ethanol | white | 61.6 | insol | water | powder-very poor film | 11 |
| 17 | PAlAmHCl/(GDL/JEFF T403 (3:1))-3% crosslinking | sodium hydroxide | water | white | 69.4 | insol | water | powder-poor, brittle film | sol. in water |
| 18 | PAlAmHCl/(GDL/JEFF T403 (3:1))-5% crosslinking | sodium hydroxide | water | white | 74.2 | insol | water | powder-poor, very brittle film | sol. in water |
| 19 | PAlAmHCl/(GDL/JEFF T403 (3:1))-20% crosslinking | sodium hydroxide | water | white | 83.9 | insol | water | powder-poor, brittle film | 83.8 |
| 20 | PAlAmHCl/(GDL/4,9-DODDA (2:1))-20% crosslinking | sodium hydroxide | water | white | 77.4 | insol | water | powder-clear film, slightly flexible, fair | 78.6 |
| 21 | PAlAmHCl/(GDL/4,9-DODDA (2:1))-25% crosslinking | sodium hydroxide | water | light yellow | 77.2 | insol | water | powder-very poor film | 26.7 |
| 22 | PAlAmHCl/(GDL/(9DA/4,9-DODDA) (2:0.5:0.5))-20% crosslinking | sodium hydroxide | water | white | 60 | — | — | Powder | 31.1 |

TABLE 1-continued

| Ex. | Composition | Catalyst | Solvent/Media | Color | % Yield | Inh Visc | Inh Sol. | Polym. Character | Swell |
|---|---|---|---|---|---|---|---|---|---|
| 23 | PAlAmHCl/(GDL/9DA (2:1))-20% crosslinking | sodium hydroxide | water | white | 63.6 | — | — | Powder | 23.7 |
| 24 | PAlAmHCl/(GDL/9DA (2:1))-15% crosslinking | sodium hydroxide | water | white | — | — | — | powder-fair film, slightly flexible | 75.2 |
| 25 | PAlAmHCl/(GDL/4,9-DODDA/9DA (2/0.5/0.5))-15% crosslinking | sodium hydroxide | water | tan | — | — | — | powder-poor, brittle film | 48.5 |
| 26 | PAlAmHCl/(GDL/4,9-DODDA (1.33:1)) | sodium hydroxide | water | tan | — | — | — | powder-poor film | 2 |
| 27 | PAlAmHCl/(GDL/9DA (1.33:1)) | sodium hydroxide | water | off white | — | — | — | powder-poor film | 1.29 |
| 28 | PAlAmHCl/(GDL/9DA (2:1))-100% crosslinking | sodium hydroxide | water | light yellow | 82.9 | — | — | Powder | 0.65 |

TABLE 2

| Ex. | Composition | Tg 1 (C.) | Tg 2 (C.) | Tg 3 (C.) | Tm 1 (C.) | ΔH (J/g) | Tm 2 (C.) | d H (J/g) | Tm 3 (C.) | d H (J/g) |
|---|---|---|---|---|---|---|---|---|---|---|
| 1 | PAlAmHCl/GDL (10:1)-20% crosslinking | — | — | — | 180.9 | — | — | — | — | — |
| 2 | PAlAmHCl/GDL (8:1)-25% crosslinking | — | — | — | 190.97 | — | — | — | — | — |
| 3 | PAlAmHCl/GDL (8.7:1)-23% crosslinking | — | — | — | 191.23 | 7.544 | — | — | — | — |
| 4 | PAlAmHCl/GDL (5:1)-40% crosslinking | — | — | — | 192.38 | 17.99 | — | — | — | — |
| 5 | PAlAmHCl/GDL (9.1:1)-22% crosslinking | — | — | — | 196.63 | 5.076 | — | — | — | — |
| 6 | PAlAmHCl/GDL (9.1:1)-22% crosslinking | — | — | — | 196.75 | 5.318 | — | — | — | — |
| 7 | PAlAmHCl/GDL (9.1:1)-22% crosslinking | — | — | — | 251.32 | 15.99 | — | — | — | — |
| 8 | PAlAmHCl/GDL (9.1:1)-22% crosslinking | — | — | — | 202.61 | 7.165 | — | — | — | — |
| 9 | PAlAmHCl/GDL (9.1:1)-22% crosslinking | — | — | — | 165.56 | 1.245 | — | — | — | — |
| 10 | PAlAmHCl/(GDL/JEFF EDR-148 (2:1))-20% crosslinking | — | — | — | 187 | 5.99 | 248.04 | 6.291 | — | — |
| 11 | PAlAmHCl/(GDL/JEFF EDR-192 (2:1))-20% crosslinking | — | — | — | — | — | — | — | — | — |
| 12 | PAlAmHCl/(GDL/JEFF T5000 (3:1))-10% crosslinking | — | — | — | 188.45 | 1.008 | 251.86 | 4.542 | — | — |
| 13 | PAlAmHCl/(GDL/JEFF T5000 (3:1))-20% crosslinking | — | — | — | 251.88 | 7.862 | — | — | — | — |
| 14 | PAlAmHCl/(GDL/JEFF T5000 (3:1))-5% crosslinking | — | — | — | 220.09 | 2.666 | — | — | — | — |
| 15 | PAlAmHCl/(GDL/JEFF T5000 (3:1))-1% crosslinking | 204.2 | — | — | — | — | — | — | — | — |
| 16 | PAlAmHCl/(GDL/JEFF T5000 (3:1))-3% crosslinking | 102.6 | 215.5 | — | — | — | — | — | — | — |
| 17 | PAlAmHCl/(GDL/JEFF T403 (3:1))-3% crosslinking | 224.4 | — | — | — | — | — | — | — | — |
| 18 | PAlAmHCl/(GDL/JEFF T403 (3:1))-5% crosslinking | 170 | 232.3 | — | — | — | — | — | — | — |
| 19 | PAlAmHCl/(GDL/JEFF T403 (3:1))-20% crosslinking | 175.7 | 227.5 | — | — | — | — | — | — | — |
| 20 | PAlAmHCl/(GDL/4,9-DODDA (2:1))-20% crosslinking | 168.8 | 234.4 | — | 204.7 | 1.281 | — | — | — | — |
| 21 | PAlAmHCl/(GDL/4,9-DODDA (2:1))-25% crosslinking | 171 | 209.5 | 247.6 | — | — | — | — | — | — |

TABLE 2-continued

| Ex. | Composition | Tg 1 (C.) | Tg 2 (C.) | Tg 3 (C.) | Tm 1 (C.) | ΔH (J/g) | Tm 2 (C.) | d H (J/g) | Tm 3 (C.) | d H (J/g) |
|---|---|---|---|---|---|---|---|---|---|---|
| 22 | PAlAmHCl/(GDL/(9DA/4,9-DODDA) (2:0.5:0.5))-20% crosslinking | 174.4 | — | — | — | — | — | — | — | — |
| 23 | PAlAmHCl/GDL/9DA (2:1))-20% crosslinking | 174.9 | — | — | — | — | — | — | — | — |
| 24 | PAlAmHCl/GDL/9DA (2:1))-15% crosslinking | 168.7 | — | — | — | — | — | — | — | — |
| 25 | PAlAmHCl/(GDL/4,9-DODDA/9DA (2/0.5/0.5))-15% crosslinking | 142.5 | 174.2 | — | 224.28 | 0.261 | — | — | — | — |
| 26 | PAlAmHCl/(GDL/4,9-DODDA (1.33:1)) | 45 | 216.6 | — | 103.33 | | 177.97 | 23.69 | 188.41 | 16.3 |
| 27 | PAlAmHCl/(GDL/9DA (1.33:1)) | 75.94 | — | — | 152.48 | 12.17 | 165.25 | 31.69 | 195.55 | 9.072 |
| 28 | PAlAmHCl/(GDL/9DA (2:1))-100% crosslinking | — | — | — | 167.03 | 4.206 | 190.61 | 14.02 | — | — |

TABLE 3

| Ex. | Composition | Tc 1 (C.) | d H (J/g) | Tc 2 (C.) | d H (J/g) | Tdec (C.) | Sol. H2O | Sol. MeOH | Sol. Toluene | Sol. DMSO | Sol. DMAC | Sol. THF | Sol. CH2CL2 |
|---|---|---|---|---|---|---|---|---|---|---|---|---|---|
| 1 | PAlAmHCl/GDL (10:1)-20% crosslinking | — | — | — | — | 200 | sol. | insol. | insol. | insol. | insol. | insol. | insol. |
| 2 | PAlAmHCl/GDL (8:1)-25% crosslinking | — | — | — | — | 200 | insol. | insol. | insol. | insol. | insol. | insol. | insol. |
| 3 | PAlAmHCl/GDL (8.7:1)-23% crosslinking | — | — | — | — | 225 | insol. | insol. | insol. | insol. | insol. | insol. | insol. |
| 4 | PAlAmHCl/GDL (5:1)-40% crosslinking | — | — | — | — | 225 | insol. | insol. | insol. | insol. | insol. | insol. | insol. |
| 5 | PAlAmHCl/GDL (9.1:1)-22% crosslinking | — | — | — | — | 200 | insol. | insol. | insol. | insol. | insol. | insol. | insol. |
| 6 | PAlAmHCl/GDL (91:1)-22% crosslinking | — | — | — | — | 225 | insol. | insol. | insol. | insol. | insol. | insol. | insol. |
| 7 | PAlAmHCl/GDL (9.1:1)-22% crosslinking | — | — | — | — | 220 | insol. | insol. | insol. | insol. | insol. | insol. | insol. |
| 8 | PAlAmHCl/GDL (9.1:1)-22% crosslinking | — | — | — | — | 210 | insol. | insol. | insol. | insol. | insol. | insol. | insol. |
| 9 | PAlAmHCl/GDL (9.1:1)-22% crosslinking | — | — | — | — | 210 | sol. | insol. | insol. | insol. | insol. | insol. | insol. |
| 10 | PAlAmHCl/(GDL/JEFF EDR-148 (2:1))-20% crosslinking | — | — | — | — | 210 | — | — | — | — | — | — | — |
| 11 | PAlAmHCl/(GDL/JEFF EDR-192 (2:1))-20% crosslinking | 223.41 | 9.953 | — | — | 210 | insol. | insol. | insol. | insol. | insol. | insol. | insol. |
| 12 | PAlAmHCl/(GDL/JEFF T5000 (3:1))-10% crosslinking | — | — | — | — | 200 | insol. | insol. | insol. | insol. | insol. | insol. | insol. |
| 13 | PAlAmHCl/(GDL/JEFF T5000 (3:1))-20% crosslinking | — | — | — | — | 210 | insol. | insol. | insol. | insol. | insol. | insol. | insol. |
| 14 | PAlAmHCl/(GDL/JEFF T5000 (3:1))-5% crosslinking | — | — | — | — | 225 | insol. | insol. | insol. | insol. | insol. | insol. | insol. |
| 15 | PAlAmHCl/(GDL/JEFF T5000 (3:1))-1% crosslinking | — | — | — | — | 250 | sol. | insol. | insol. | insol. | insol. | insol. | insol. |
| 16 | PAlAmHCl/(GDL/JEFF T5000 (3:1))-3% crosslinking | — | — | — | — | 235 | insol. | insol. | insol. | insol. | insol. | insol. | insol. |
| 17 | PAlAmHCl/(GDL/JEFF T403 (3:1))-3% crosslinking | — | — | — | — | 240 | sol. | insol. | insol. | insol. | insol. | insol. | insol. |
| 18 | PAlAmHCl/(GDL/JEFF T403 (3:1))-5% crosslinking | — | — | — | — | 240 | sol. | insol. | insol. | insol. | insol. | insol. | insol. |
| 19 | PAlAmHCl/(GDL/JEFF T403 (3:1))-20% crosslinking | — | — | — | — | 225 | insol. | insol. | insol. | insol. | insol. | insol. | insol. |
| 20 | PAlAmHCl/(GDL/4,9-DODDA (2:1))-20% crosslinking | — | — | — | — | 200 | insol. | insol. | insol. | insol. | insol. | insol. | insol. |

TABLE 3-continued

| Ex. Composition | Tc 1 (C.) | d H (J/g) | Tc 2 (C.) | d H (J/g) | Tdec (C.) | Sol. H2O | Sol. MeOH | Sol. Toluene | Sol. DMSO | Sol. DMAC | Sol. THF | Sol. CH2CL2 |
|---|---|---|---|---|---|---|---|---|---|---|---|---|
| 21 PAlAmHCl/(GDL/4,9-DODDA (2:1))-25% crosslinking | 284.77 | 1.116 | — | — | 200 | insol. | insol. | insol. | insol. | insol. | insol. | insol. |
| 22 PAlAmHCl/(GDL/(9DA/4,9-DODDA) (2:0.5:0.5))-20% crosslinking | — | — | — | — | 225 | insol. | insol. | insol. | insol. | insol. | insol. | insol |
| 23 PAlAmHCl/(GDL/(9DA (2:1))-20% crosslinking | — | — | — | — | 225 | insol. | insol. | insol. | insol. | insol. | insol. | insol. |
| 24 PAlAmHCl/(GDL/(9DA (2:1))-15% crosslinking | — | — | — | — | 225 | insol. | insol. | insol. | insol. | insol. | insol. | insol. |
| 25 PAlAmHCl/(GDL/4,9-DODDA/9DA (2/0.5/0.5))-15% crosslinking | — | — | — | — | 175 | insol. | insol. | insol. | insol. | insol. | insol. | insol. |
| 26 PAlAmHCl/(GDL/4,9-DODDA (1.33:1)) | — | — | — | — | 150 | insol. | insol. | insol. | insol. | insol. | insol. | insol. |
| 27 PAlAmHCl/(GDL/(9DA (1.33:1)) | — | — | — | — | 150 | insol. | insol. | insol. | insol. | insol. | insol. | insol. |
| 28 PAlAmHCl/(GDL/(9DA (2:1))-100% crosslinking | — | — | — | — | 150 | — | — | — | — | — | — | — |

Example 29

Synthesis of Modified Polyallylamine Crosslinked with GDL

Into a 2000-mL 3-necked flask equipped with a heating mantle, reflux condenser, nitrogen inlet, and overhead stirrer was added 525 mL of water, 70 g of polyallylamine hydrochloride (0.749 mole equivalent of amine), and 2.24 g (0.056 mol) of sodium hydroxide. After these ingredients dissolved, 17.08 g (0.056 mol) of 1-bromohexadecane was added. The reaction mixture was heated at reflux for 5 hours. Afterward, the reaction mixture was cooled to room temperature and stirred overnight. An additional 5.60 g (0.140 mol) of sodium hydroxide was added to the mixture. After the sodium hydroxide dissolved, 12.18 g (0.070 mol) of GDL dissolved in 175 mL of water was added to the reaction mixture. Almost immediately a gel formed. The gelled mixture was then gently heated at 50° C. for about 7 hours. The gel was filtered, washed 3× with methanol, and then washed 3× with THF. It was then put into a vacuum oven set at 80° C. for at 24 hours to dry the polymer. The pale yellow polymer (58.85 g, 60.5%) exhibited a swell ratio of 7.9.

Example 30A

Synthesis of Polyallylamine Crosslinked with Diethyl Tartrate

The preparation was conducted under nitrogen atmosphere with oven-dried glassware. Polyallylamine hydrochloride (MW ca. 60,000, 0.876 g, 9.36 mmol) was weighed into a 20-mL scintillation vial equipped with a magnetic stirbar, and water (2 mL) was added. Dropwise addition of an aqueous solution (1.0 mL) of sodium hydroxide (0.113 g, 2.83 mmol) to the solution resulted in a viscous solution. A solution of diethyl L-tartrate (0.240 mL, 1.40 mmol) in water (1.0 mL) was added and the resulting solution was stirred at ambient temperatures for 38 hours. The gelled reaction mixture was washed with methanol (160 mL) to remove sodium chloride. Vacuum-drying gave a white solid (0.86 g, 93% yield) that exhibited a swell ratio of 112.6 (determined after swollen gel was subjected to 6 hours of dynamic suction followed by ~28 hours of static suction).

Example 30B

Synthesis of Polyallylamine Crosslinked with Diethyl Tartrate

Poly(allylamine hydrochloride), $M_w$ 60,000 (42.04 g, 0.4493 mole of amine groups) was dissolved overnight in 155 mL of water in a 3-neck 500-mL round-bottom flask equipped with a magnetic stir bar. A solution of 5.392 g (0.1348 mole) of sodium hydroxide in 25 mL of water was added dropwise over a period of 10 minutes, using 2 mL of water to complete the transfer. To the resulting pale yellow syrup was added with stirring a solution of 13.897 g (67.40 mmoles) of diethyl L-tartrate in 10 mL of water, using 2 mL of water to complete the transfer. The reaction was allowed to proceed for 4 days, during which the mixture gelled and the magnetic stir bar seized. The reaction mixture was combined with 250 mL of methanol to precipitate out the product. The resulting gummy solid was separated from the liquid and triturated in a blender with 8 successive 250-mL portions of methanol, decanting the methanol each time. The resulting solid was ground and dried under vacuum to give 38.47 g (86% yield) of hydrogel that exhibited a swell factor of 224.

Example 31

Synthesis of Polyallylamine Crosslinked with GDL

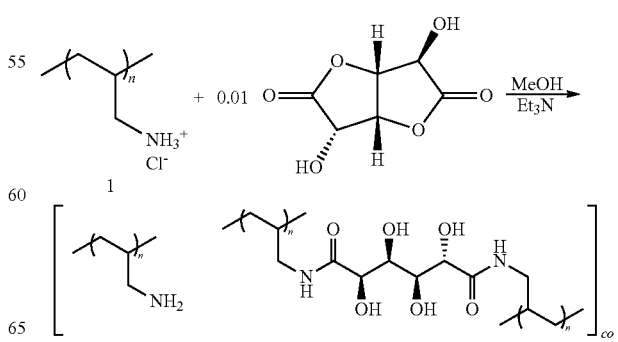

The preparation was conducted in a drybox with oven-dried glassware. Polyallylamine hydrochloride (MW ca. 60,000, 6.88 g, 73.5 mmol) was weighed into a 500-mL round-bottom flask equipped with a magnetic stirbar. Methanol (285 mL) was added and the solution was treated with neat triethylamine (12.3 mL, 88.3 mmol) followed by dropwise addition of a solution of GDL (0.13 g, 0.74 mmol) in methanol (10 mL). The resulting solution was stirred at ambient temperature for four days. Most of the reaction solvent was decanted, and the remaining reaction mixture was filtered and vacuum-dried to give a white solid (1.00 g, 23% yield) that exhibited a swell ratio of 22.8. When the swell test was repeated, allowing 19 hours for the gel to swell followed by 2 hours of dynamic suction and 9 hours of static suction, the swell ratio was 22.4. After 14 hours' exposure to ambient atmosphere, the sample retained 19.9 times its own weight in water.

Example 32A

Synthesis of Polyallylamine Crosslinked with N,N'-Bis(ethoxycarbonylmethyl)-D-glucaramide

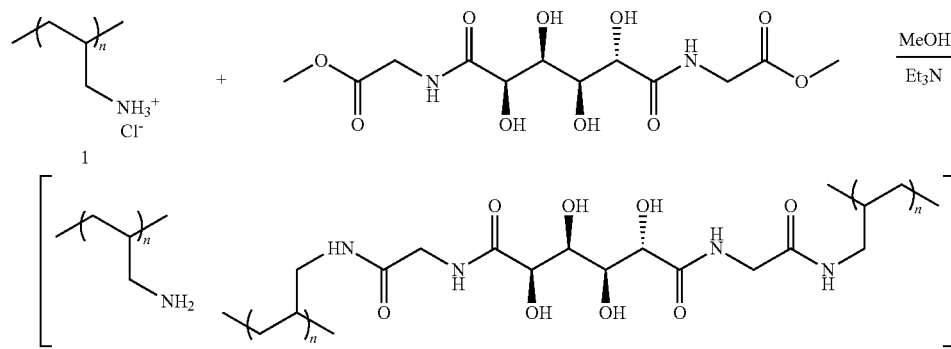

Preparation was conducted in a drybox with oven-dried glassware. Polyallylamine hydrochloride (MW ca. 60,000, 6.55 g, 70.0 mmol) was weighed into a 500-mL round-bottom flask equipped with a magnetic stirbar. Methanol (270 mL) was added and the solution was treated with neat triethylamine (11.7 mL, 84.0 mmol) followed by a slurry of N,N'-bis(methoxycarbonylmethyl)-D-glucaramide (0.25 g, 0.69 mmol) in methanol (20 mL). The resulting solution was stirred at ambient temperature for four days. The reaction solvent was removed under vacuum, and the oily solid was washed repeatedly with methanol (180 mL). Addition of pentane (50 mL) to a methanol slurry (ca. 20 mL volume) produced a solid that was filtered and then vacuum-dried to give a white solid (2.39 g, 57% yield) that exhibited a swell ratio (after 29 minutes of suction) of 62.8. When the swell test was repeated, allowing 16 hours for the gel to swell followed by 34 minutes of suction, the swell ratio was 118.9. After 23 hours' exposure to ambient atmosphere, the sample retained 108.6 times its own weight in water.

Example 32B

Synthesis of Polyallylamine Crosslinked with N,N'-Bis(ethoxycarbonylmethyl)-D-glucaramide To 23.03 g (0.2463 mole of amine groups) of poly(allylamine hydrochloride), $M_w$ 60,000, in 950 mL of dry methanol in a 2-L round-bottom flask under nitrogen were added 41.2 mL (0.296 mole) of triethylamine over 30 minutes. A slurry of N,N'-bis(ethoxycarbonylmethyl)-D-glucaramide in a total of 65 mL of dry methanol was then added. The mixture was stirred at ambient temperature for 5 days and then concentrated under reduced pressure to about 150 mL. The resulting solid was separated from the methanol, washed repeatedly with methanol and then dried under vacuum to give 12.92 g (88% yield) of hydrogel that exhibited a swell factor of 125.

Example 33

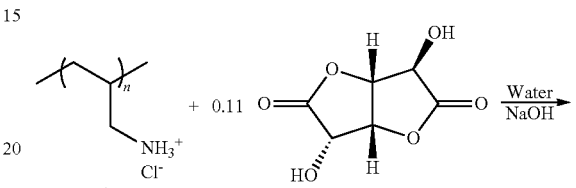

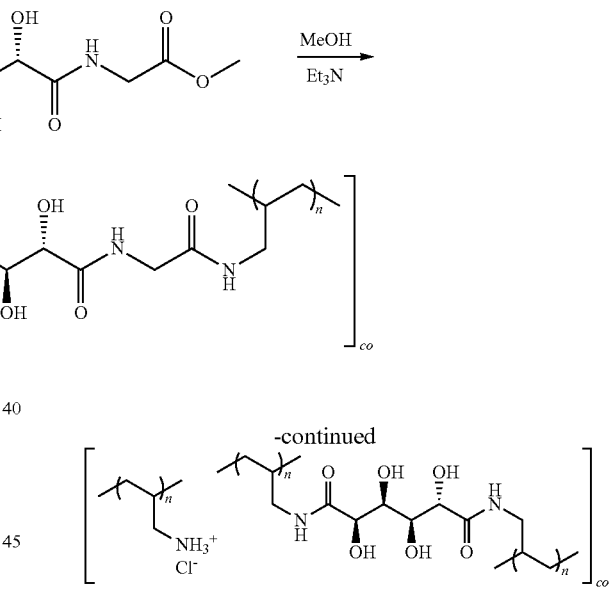

Polyallylamine hydrochloride (MW ca. 60,000, 2.84 g, 30.4 mmol) was weighed into 100-mL round-bottom flask equipped with a magnetic stirbar. Water (16 mL) was added and the solution was treated with an aqueous (4 mL) solution of sodium hydroxide (0.27 g, 6.67 mmol) followed by a solution of GDL (0.58 g, 3.34 mmol) in water (10 mL). The reaction solution was stirred overnight at ambient temperature resulting in a gel-like mixture. The gel was washed with four 50-mL portions of methanol and then vacuum-dried to give a white solid (2.26 g, 69% yield) that exhibited a swell ratio (after 2 hours of suction) of 186.5. After 3 additional days' exposure to static suction, the sample retained 67.9 times its own weight in water. When the swell test was repeated with the same sample, allowing 5 hours for the gel to swell followed by 2 hours of dynamic suction and 24 hours of static suction, the swell ratio was 206.0. After 3 and 8 days' additional exposure to static suction, the sample retained 173.8 and 65.5 times its own weight in water, respectively.

Example 34

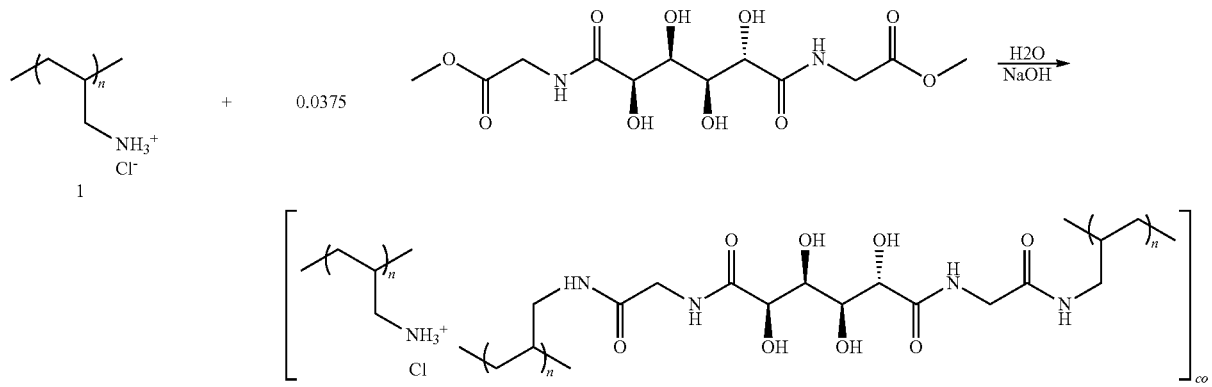

Preparation was conducted under nitrogen atmosphere with oven-dried glassware. Polyallylamine hydrochloride (MW ca. 60,000, 1.01 g, 10.8 mmol) was weighed into a 20-mL scintillation vial equipped with a magnetic stirbar, and water (2 mL) was added. Dropwise addition to the slurry of an aqueous solution (1.0 mL) of sodium hydroxide (0.033 g, 0.83 mmol) resulted in a viscous solution. A solution of N,N'-bis(methoxycarbonylmethyl)-D-glucaramide (0.14 g, 0.41 mmol) in water (1.5 mL) was added, and the resulting solution was stirred at ambient temperature for 45 hours. Solvent was removed under vacuum from the gelled reaction mixture, and the solid was washed with methanol (125 mL) to remove sodium chloride. Vacuum-drying gave a white solid (0.98 g, 89% yield) that exhibited a swell ratio (after 5 minutes of dynamic suction and 45 minutes of static suction) of 105.8. After 2 days' exposure to ambient atmosphere, the sample retained 96.5 times its own weight in water. When the swell test was repeated with the same sample, allowing 4.5 hours for the gel to swell followed by 5 hours of dynamic suction and 14 hours of static suction, the swell ratio was 197.6. After 6 days' exposure to ambient atmosphere, the sample retained 167.8 times its own weight in water.

Example 35

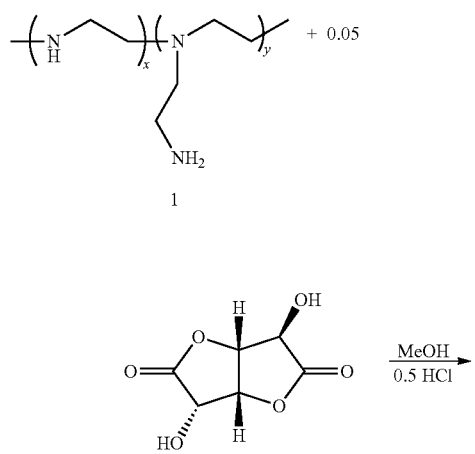

-continued

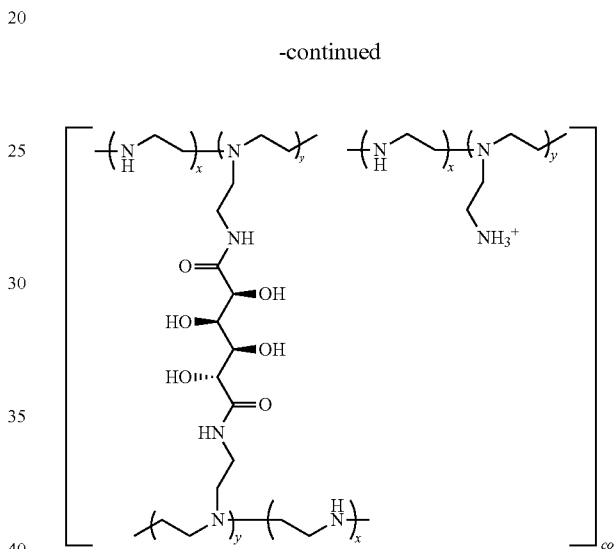

Polyethylenimine ($M_n$=ca. 10,000, $M_w$=ca. 25,000, Aldrich 408727, 0.74 g, 17.2 mmol) was weighed into a 20-mL scintillation vial equipped with a magnetic stirbar, and methanol (4.5 mL) was added. Concentrated hydrochloric acid (0.72 mL, 8.65 mmol) was added to the reaction solution dropwise over ca. one minute and the mixture was stirred at ambient temperature for 3 hours. A solution of GDL (0.15 g, 0.862 mmol) in methanol (1 mL) was added dropwise over ca. one minute to the reaction solution. The reaction mixture began to gel after 3 hours, but stirring was continued for 24 hours. The solvent was removed under vacuum and the solid was vacuum-dried to give a yellow solid (ca. 0.2 g) that exhibited a swell ratio (after 1 hour of static suction) of 24.1. After 5 days' exposure to ambient atmosphere, the sample retained 9.2 times its own weight in water. When the swell test was repeated with the same sample, allowing 7.5 hours for the gel to swell followed by 35 minutes of dynamic suction, the swell ratio was 36.6. After 1 day's exposure to ambient atmosphere, the sample retained 34.2 times its own weight in water.

Example 36

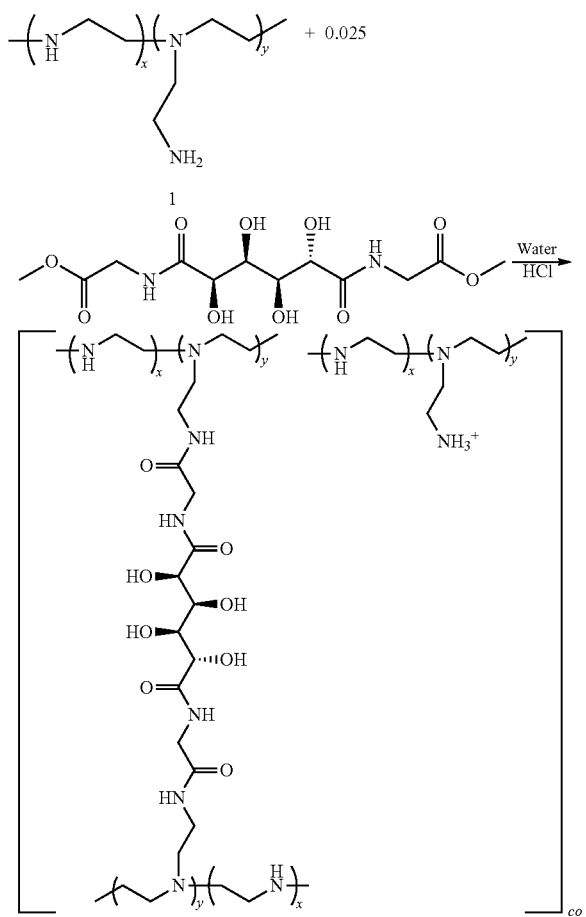

Polyethylenimine ($M_n$=ca. 10,000, $M_w$=ca. 25,000, Aldrich 408727, 0.67 g, 15.6 mmol) was weighed into a 20-mL scintillation vial equipped with a magnetic stirbar, and water (2.5 mL) was added. Concentrated hydrochloric acid (0.65 mL) was added dropwise to the solution followed by solid N,N'-bis(methoxycarbonylmethyl)-D-glucaramide (0.14 g, 0.39 mmol) and water (1 mL). The reaction solution was stirred for 5 days at ambient temperature. The solvent was then removed under vacuum, and the solid was vacuum-dried to give a colorless solid that exhibited a swell ratio (after 50 minutes of dynamic suction and 15 minutes of static suction) of 17.6. When the swell test was repeated with the same sample, allowing 15 hours for the gel to swell followed by 2.25 hours of suction, the swell ratio was 25.5. After five days' exposure to ambient atmosphere, the sample retained 22.8 times its own weight in water.

Example 37

Biocidal Activity of Crosslinked Hydrogels

Antimicrobial activity was determined by a standard micro-shake flask test. Bacterial cultures were inoculated into TSB (Trypticase Soy Broth) and incubated at 37° C. overnight for 20+/−2 hours. The following day, the concentration of bacteria was adjusted to ~$1.0 \times 10_5$ cfu/mL (cfu=colony forming unit) by dilution with 0.6 mM phosphate buffer. Diluted bacterial culture (2.5 mL) was then transferred into culture plate wells containing 2.5 mL of hydrogel (~50 mg of solid dispersed in 2.5 mL of 0.6 mM phosphate buffer) or just 2.5 mL of 0.6 mM phosphate buffer (control). The culture plates were incubated at room temperature on a platform shaker with constant shaking motion. Three 100-µL aliquots were periodically removed from each well and serially diluted with 0.6 mM phosphate buffer. Undiluted and diluted samples from each well were plated onto duplicate TSA (trypticase soy agar) plates, and incubated at 37° C. for 20±2 hrs. After incubation, the number of bacterial colonies on each plate was counted using a Q-count instrument or equivalent counting method. The colony count was averaged and normalized by correcting for the dilution factor and reported as the number of colony forming units (cfu) per mL. Log reduction (log rdxn)=(mean $\log_{10}$ density of microbes in flasks of untreated control samples)−(mean $\log_{10}$ density of microbes in flasks of treated samples).

Microbes tested were *Escherichia coli*, *Pseudomonas aeruginosa*, *Stapphyiococcus aureus*, and *Candida albicans*.

Three hydrogel samples were tested for antimicrobial activity: Sample A was prepared as in Example 29. Sample B was prepared in the manner of Example 30A. Sample C was prepared as in Example 31. Results are in Table 4.

TABLE 4

Biocidal Activity of Crosslinked Hydrogels

| | | | | sample | | | | | |
|---|---|---|---|---|---|---|---|---|---|
| | | | | A | | B | | C | |
| microbe | t, h | hydrogel wt % | inoculum (control) log cfu | log cfu | log rdxn | log cfu | log rdxn | log cfu | log rdxn |
| E. coli | 4 | 1.0 | 4.86 | 1.37 | 3.49 | 0.00 | 4.86 | 0.00 | 4.86 |
| | | 0.50 | 4.86 | 1.73 | 3.13 | 0.00 | 4.86 | 0.00 | 4.86 |
| | | 0.25 | 4.86 | 1.70 | 3.16 | 0.00 | 4.86 | 0.00 | 4.86 |
| | | 0.10 | 4.86 | 2.22 | 2.64 | 0.00 | 4.86 | 0.00 | 4.86 |
| | 24 | 1.0 | 4.86 | 0.00 | 4.86 | | | | |
| | | 0.50 | 4.86 | 0.00 | 4.86 | | | | |
| | | 0.25 | 4.86 | 0.00 | 4.86 | | | | |
| | | 0.10 | 4.86 | 0.00 | 4.86 | | | | |
| P. aeruginosa | 4 | 1.0 | 4.86 | 0.00 | 4.86 | 0.00 | 4.86 | 0.00 | 4.86 |
| | | 0.50 | 4.86 | 0.00 | 4.86 | 0.00 | 4.86 | 0.00 | 4.86 |
| | | 0.25 | 4.86 | 0.00 | 4.86 | 0.00 | 4.86 | 0.00 | 4.86 |
| | | 0.10 | 4.86 | 0.00 | 4.86 | 0.00 | 4.86 | 0.00 | 4.86 |
| S. aureus | 4 | 1.0 | 4.66 | 3.94 | 0.72 | 0.00 | 4.66 | 0.00 | 4.66 |
| | | 0.50 | 4.66 | 3.92 | 0.74 | 0.00 | 4.66 | 0.00 | 4.66 |

TABLE 4-continued

Biocidal Activity of Crosslinked Hydrogels

| | | | | sample | | | | | |
|---|---|---|---|---|---|---|---|---|---|
| | | | | A | | B | | C | |
| microbe | t, h | hydrogel wt % | inoculum (control) log cfu | log cfu | log rdxn | log cfu | log rdxn | log cfu | log rdxn |
| | | 0.25 | 4.66 | 3.51 | 1.15 | 0.00 | 4.66 | 0.00 | 4.66 |
| | | 0.10 | 4.66 | 3.47 | 1.19 | 0.00 | 4.66 | 0.00 | 4.66 |
| | 24 | 1.0 | 4.66 | 2.40 | 2.26 | | | | |
| | | 0.50 | 4.66 | 1.37 | 3.29 | | | | |
| | | 0.25 | 4.66 | 1.18 | 3.49 | | | | |
| | | 0.10 | 4.66 | 1.67 | 2.99 | | | | |
| C. albicans | 4 | 1.0 | 5.09 | 0.00 | 5.09 | 0.00 | 5.09 | 0.00 | 5.09 |
| | | 0.50 | 5.09 | 0.00 | 5.09 | 0.00 | 5.09 | 0.00 | 5.09 |
| | | 0.25 | 5.09 | 0.00 | 5.09 | 0.00 | 5.09 | 0.00 | 5.09 |
| | | 0.10 | 5.09 | 1.92 | 3.17 | 0.00 | 5.09 | 0.00 | 5.09 |

Example 38

Emulsion Prepared Using Hydrogel Prepared from Polyallylamine HCl, GDL, and Jeffamine® EDR-192

A crosslinked hydrogel was prepared in the following manner: 28.0 g (0.30 equiv of polyallylamine hydrochloride was dissolved in 200 mL of water along with 2.4 g (0.06 mol) of sodium hydroxide. To that solution was added a solution of 5.2 g (0.030 mol) of GDL and 2.9 g (0.015 mol) of Jeffamine® EDR-192 dissolved in 100 mL of water. The mixture was then heated to 50° C. Within 1 hour, a gelled product had formed. The gel was left to "cure" overnight at room temperature. It was then filtered and washed 3 times with MeOH/THF. The remaining polymer was then dried in a vacuum oven at 80° C. to yield 20.63 g (61%) of a white granular material. The polymer exhibited a swell ratio of 81.

An emulsion was prepared using 2.0 g of the polymer prepared above, 17.0 g of octyl palmitate, and 148 mL of water. These ingredients were added to a 250-mL beaker and emulsified using a Silverson Lab Mixer equipped with a rotor-stator square-holed blade running at 5,000 rpm for 5 min. A thick, creamy white emulsion was prepared. After 8 months' storage in a jar at room temperature, separation of the emulsion was negligible.

Example 39

Preparation of Crosslinked Polymer using Poly(methacryloyl chloride), GDL, and Ethylenediamine Into a 250-mL 3-necked round-bottom flask equipped with a heating mantle, reflux condenser, nitrogen inlet, and overhead stirrer was added a 25 mL of dioxane containing 6.25 g (0.598 equivalent) of poly(methacryloyl chloride) (Polysciences, Inc., Warrington, Pa.). To this solution was added 3.5 g (0.0150 mol) of N,N'-bis(2-aminoethyl)-D-glucaramide (prepared by reacting 10 equivalents of ethylenediamine with GDL in DMAC at 50° C. and isolating the product as a white precipitate). The mixture was stirred and heated at 50° C. over a period of 21 hours. During this time, a slight color change from brown to yellow was noted; however, it did not appear that the diaminodiamide was ever fully solubilized in the dioxane solvent. The resulting product was poured into THF, filtered, and washed 3 times with THF to yield 2.65 g (27%) of a light tan solid material; $Tg_1$ 49.67° C.; $Tg_2$ 64.14° C.; $T_{dec}$ 175° C.-onset; $\eta_{inh}$ (HFIP) insol.

Example 40

Synthesis of Chitosan Crosslinked with GDL

Chitosan (Primex TM-656, MW ca. 79,000, 95% deacetylated, 0.79 g, 4.90 mmol) was weighed into a 20-mL scintillation vial equipped with a magnetic stirbar. Water (11.5 mL) was added, and the mixture was stirred for 15 minutes at ambient temperature. A solution of hydrochloric acid (37%, 0.29 mL, 3.45 mmol) in water (1.5 mL) was added dropwise, and the resulting viscous light yellow mixture was stirred for 15 minutes at ambient temperature. A freshly prepared solution of GDL (0.09 g, 5.40 mmol) in water (1.5 mL) was added dropwise, and the reaction mixture was stirred for 38 hours at ambient temperature, resulting in a tan-colored homogeneous gel-like mixture. Approximately 5 mL of the solvent was removed under vacuum and the reaction mixture was transferred to a round-bottom flask with 15 mL of tetrahydrofuran. The resulting precipitate was washed with four 30-mL portions of tetrahydrofuran then vacuum-dried to give a white solid (0.75 g) that had a swell ratio of 3.

Example 41

Hard Surface Disinfection by Crosslinked Hydrogels

Tests were performed by Consumer Product Testing Company, Fairfield, N.J. following Association of Official Analytical Chemists (AOAC) Use Dilution test methods 955.14 and 955.15.

Hydrogel A was prepared by reacting poly(allylamine hydrochloride), M, 60,000, with 0.15 mole equivalent (relative to amine groups) of diethyl L-tartrate according to Example 30B to give a polymer nominally having 30% of its amine groups crosslinked. Hydrogel B was prepared by reacting poly(allylamine hydrochloride), M, 60,000, with 0.01 mole equivalent (relative to amine groups) of N,N'-bis(ethoxycarbonylmethyl)-D-glucaramide according to Example 32B to give a polymer nominally having 2% of its amine groups crosslinked. Each hydrogel was dispersed in deionized water, hydrogel A at 0.5 wt % (w/v) and hydrogel B at 1 wt % (w/v).

Type 304 stainless steel penicylinders (8 mm OD, 6 mm ID, 10 mm L) were soaked overnight in 1N sodium hydroxide, washed with water until the rinse water was neutral to phenolphthalein, and autoclaved in 0.1% w/v aqueous asparagine solution. The sterile penicylinders were drained and transferred aseptically into a 48-hour culture broth (1 mL per cylinder) of *Staphylococcus aureus* (ATCC #6538) or *Salmonella choleraesuis* (ATCC #10708). After being immersed in culture broth for 15 minutes, the penicylinders were drained and transferred by sterile hook into a sterile glass petri dish lined with sterile filter paper so that the cylinders stood on end without touching one another. The penicylinders were dried at 37° C. for 40 minutes.

For each hydrogel tested, 10 penicylinders inoculated with a given test organism were immersed individually for 10 minutes at 20° C. in 10 mL of aqueous hydrogel dispersion. Each penicylinder was then removed from the hydrogel dispersion, drained, and deposited into a primary culture tube containing 10 mL of Letheen broth and incubated at 37° C. After 30 minutes, each penicylinder was transferred into secondary culture tube containing 10 mL of Letheen broth, and both primary and secondary culture tubes were incubated at 37° C. for 48 hours, after which they were examined for microbial growth as evidenced by turbidity.

Neutralization of each antimicrobial hydrogel by double serial subculture was shown to be effective by inoculating tubes showing no growth with low levels of test organism. Viability of test organisms was demonstrated by incubating inoculated penicylinders in deionized water instead of a hydrogel suspension.

Results in Table 5 demonstrate that hydrogel B is bactericidal against *Staphylococcus aureus*. While it is also active against *Salmonella choleraesuis*, hydrogel B does not completely eradicate viable *Salmonella choleraesuis* under the conditions employed.

TABLE 5

Use Dilution Test Results. Number of Penicylinders Showing Residual Microbial Activity after 10-Minute Exposure to Hydrogel

| hydrogel[a] | wt %[b] | *Staphylococcus aureus* primary | *Staphylococcus aureus* secondary | *Salmonella choleraesuis* primary | *Salmonella choleraesuis* secondary |
|---|---|---|---|---|---|
| A | 0.5 | 10/10 | 10/10 | 10/10 | 10/10 |
| B | 1.0 | 0/10 | 0/10 | 3/10 | 3/10 |

[a]See text of Example 41 for descriptions of hydrogels A and B.
[b]Loading of hydrogel (w/v) in aqueous dispersion.

Example 42

Preservation of a Skin Cream by a Crosslinked Hydrogel

Skin creams were formulated by mixing ingredients in the amounts listed in Table 6. The crosslinked hydrogel used was made according to Example 30B.

Ingredients of Phase I were combined and heated to 77° C. Ingredients of Phase 2 were combined and heated to 77° C. While Phase 1 was kept at 77° C. and vigorously agitated by an overhead stirrer, Phase 2 was added to Phase 1. After 15 minutes of vigorous agitation at 77° C., triethanolamine was added to the mixture. After the mixture had been vigorously agitated at 77° C. for an additional 15 to 25 minutes, external heating was discontinued, and the vigorously agitated mixture was allowed to cool. When the temperature of the mixture reached 37 to 38° C., Dow Corning 2001 fluid dimethicone was added, the speed of agitation was reduced, and the mixture was allowed to cool to room temperature.

TABLE 6

Skin Cream Formulations

| ingredient | formulation A (control) | formulation B |
|---|---|---|
| Phase 1 | | |
| deionized water | 70.0 g | 69.3 g |
| crosslinked hydrogel | 0.0 g | 1.0 g |
| Phase 2 | | |
| octamethylcyclotetrasiloxane | 20.0 g | 19.8 g |
| Abil ® EM-90 cetyl dimethicone copolyol | 2.0 g | 2.0 g |
| Stepan TAB-2 ® | 3.0 g | 3.0 g |
| Phase 3 | | |
| triethanolamine | 2.4 g | 2.4 g |
| Dow Corning 200 ® fluid dimethicone | 2.5 g | 2.5 g |

Ten grams of each skin cream formulation were supplemented with 500 µL of trypticase soy broth, mixed in by hand, to promote bacterial growth. Each skin cream sample was then inoculated with 100 µL of a 1:10 dilution of an overnight culture of *Pseudomonas aeruginosa* and 100 µL of a 1:10 dilution of an overnight culture of *Staphylococcus aureus*, yielding a bacterial load of approximately $1\times10^6$ cfu/g for each organism (cfu=colony forming unit). Periodically, each inoculated skin cream was sampled with a 10-µL loop, which was then streaked onto a trypticase soy agar (TSA) plate. Plates were incubated at 37° C. for 24 hours and then examined for bacterial growth.

Results in Table 7 show that bacteria persisted in the unpreserved control sample, A, but not in the sample containing crosslinked hydrogel, B.

TABLE 7

Bacterial Growth Observed After Streaking on TSA Plates

| time, days | skin cream formulation A (control) | skin cream formulation B |
|---|---|---|
| 0 | heavy | heavy |
| 0.25 | heavy | heavy |
| 1 | heavy | 10-100 cfu |
| 7 | moderate-heavy | none |

Example 42A

Preservation of a Skin Cream by a Crosslinked Hydrogel

Microbiological tests were performed by Consumer Product Testing Company, Fairfield, N.J. according to the United States Pharmacopoeia (USP), 24th Edition, <51> Antimicrobial Effectiveness Testing.

Hydrogel A was prepared by reacting poly(allylamine hydrochloride), $M_w$ 60,000, with 0.15 mole equivalent (relative to amine groups) of diethyl L-tartrate according to Example 30B to give a polymer nominally having 30% of its amine groups crosslinked. Hydrogel B was prepared by reacting poly(allylamine hydrochloride), $M_w$ 60,000, with 0.01 mole equivalent (relative to amine groups) of N,N'-bis (ethoxycarbonylmethyl)-D-glucaramide according to Example 32B to give a polymer nominally having 2% of its amine groups crosslinked.

Skin creams were formulated by mixing ingredients in the amounts listed in Table 8. Ingredients of Phase 1 were combined and heated to 77° C. Ingredients of Phase 2 were combined and heated to 77° C. While Phase 1 was kept at 77° C. and vigorously agitated by an overhead stirrer, Phase 2 was added to Phase 1. After 15 minutes of vigorous agitation at 77° C., triethanolamine was added to the mixture. After the mixture had been vigorously agitated at 77° C. for an additional 15 to 25 minutes, external heating was discontinued, and the vigorously agitated mixture was allowed to cool. When the temperature of the mixture reached 37 to 38° C., Dow Corning 200® fluid dimethicone was added, the speed of agitation was reduced, and the mixture was allowed to cool to room temperature.

agar (TSA) plates incubated at 20 to 25° C. for 3 days for bacteria and Sabouraud dextrose agar (SDA) plates incubated at 20 to 25° C. for 5 days for the fungi.

Results in Table 9 demonstrate that the hydrogels increase the rate of kill of gram positive (*S. aureus*) and gram negative (*E. coli, P. aeruginosa*) bacteria and yeast (*C. albicans*) in a skin cream formulation. No activity against mold (*A. niger*) was demonstrated by the two hydrogel compositions tested.

TABLE 9

Log (CFU/g) for Microorganisms in Skin Cream Formulations

| | test microorganism | | | | | | | | | | | | | | |
|---|---|---|---|---|---|---|---|---|---|---|---|---|---|---|---|
| | S. aureus | | | E. coli | | | P. aeruginosa | | | C. albicans | | | A. niger | | |
| | | | | | | | skin cream formulation | | | | | | | | |
| day | 1 | 2 | 3 | 1 | 2 | 3 | 1 | 2 | 3 | 1 | 2 | 3 | 1 | 2 | 3 |
| 0 | 5.91 | 5.91 | 5.91 | 6.04 | 6.04 | 6.04 | 5.99 | 5.99 | 5.99 | 5.96 | 5.96 | 5.96 | 5.79 | 5.79 | 5.79 |
| 7 | 3.34 | <1 | <1 | 3.88 | 2.57 | 2.46 | 3.70 | 2.15 | 2.60 | 3.56 | 2.28 | 2.08 | 5.08 | 5.20 | 5.04 |
| 14 | 2.70 | <1 | <1 | 2.15 | <1 | <1 | 1.00 | <1 | 2.43 | 2.67 | <1 | <1 | 5.04 | 5.18 | 4.98 |
| 28 | <1 | <1 | <1 | <1 | <1 | <1 | <1 | <1 | <1 | 2.66 | <1 | <1 | 3.45 | 4.15 | 4.58 |

TABLE 8

Skin Cream Formulations

| | formulation | | |
|---|---|---|---|
| ingredient | 1 (control) | 2 | 3 |
| Phase 1 | | | |
| deionized water | 350.5 g | 346.5 g | 207.9 g |
| crosslinked hydrogel A | — | 5.0 g | — |
| crosslinked hydrogel B | — | — | 3.0 g |
| Phase 2 | | | |
| octamethylcyclotetrasiloxane | 100.0 g | 99.0 g | 59.4 g |
| Abil ® EM-90 cetyl dimethicone copolyol | 10.0 g | 10.0 g | 6.0 g |
| Stepan TAB-2 ® | 15.0 g | 15.0 g | 9.0 g |
| Phase 3 | | | |
| triethanolamine | 12.0 g | 12.0 g | 7.2 g |
| Dow Corning 200 ® fluid dimethicone | 12.5 g | 12.5 g | 7.5 g |

The microbial tests described below were performed by Consumer Product Testing Company, Fairfield, N.J. Twenty-gram portions of each skin cream formulation were aseptically transferred into sterile glass containers and inoculated with 100 μL of a 1×10⁸ cfu/mL culture of *Staphylococcus aureus* (ATCC #6538), *Escherichia coli* (ATCC #8739), *Pseudomonas aeruginosa* (ATCC #9027), *Candida albicans* (ATCC #10231) or *Aspergillus niger* (ATCC #16404), yielding a microbial load between 1×10⁵ and 1×10⁶ cfu/g. Inoculated samples were incubated at 20 to 25° C. protected from light. Periodically, samples of each inoculated skin cream were serially diluted tenfold, and microbial counts were determined by the pour plate method, using trypticase soy Example 43

Human Repeat Insult Patch Test of Crosslinked Hydrogels

Hydrogel A was prepared by reacting poly(allylamine hydrochloride), $M_w$ 60,000, with 0.15 mole equivalent (relative to amine groups) of diethyl L-tartrate according to Example 30B to give a polymer nominally having 30% of its amine groups crosslinked. Hydrogel B was prepared by reacting poly(allylamine hydrochloride), $M_w$ 60,000, with 0.01 mole equivalent (relative to amine groups) of N,N'-bis(ethoxycarbonylmethyl)-D-glucaramide according to Example 32B to give a polymer nominally having 2% of its amine groups crosslinked. Each hydrogel was dispersed in deionized water, hydrogel A at 0.5 wt % (w/v) and hydrogel B at 0.8 wt % (w/v).

The Repeat insult Patch Test was performed by Consumer Product Testing Company, Fairfield, N.J. The fifty-two subjects completing this test included 12 men, age 32 to 68 years, and 40 women, age 22 to 79 years. Subjects had no visible skin disease, were in good health, were not pregnant or nursing, were not under a doctor's care or taking medication that would influence the outcome of the study, and had not used a topical or systemic steroid or antihistamine for at least seven days prior to beginning the study.

Approximately 0.2 mL of each hydrogel dispersion, or an amount sufficient to cover the contact surface, was applied to the ¾"×¾" absorbent pad of an adhesive dressing. The dressing was then applied to a marked spot between the scapulae of each subject, thus forming an occlusive patch. Patches were applied to the same site three times a week (typically, Monday, Wednesday, and Friday) for three consecutive weeks (total of 9 applications). Each patch was removed after 24 hours of contact. The site of application was examined and scored upon removal of the first patch and again 24 hours after removal of the first patch. Thereafter, the site of application was examined and scored 24 or 48 hours after the removal of each patch, usually just before application of the subsequent patch. Thus, the application site on each subject was examined 10 times during the Induction Phase. Approximately 2 weeks after application of the final Induction patch, a Challenge patch was applied to a virgin site adjacent to the original site, following the same procedure as described above. The patch was removed 24 hours after application, and the site was examined and scored. The Challenge site was examined and scored again 48 hours after removal of the Challenge patch.

Each time an Induction or Challenge site was examined, it was scored according to the following scale: 0=no visible skin reaction, +=barely perceptible or spotty erythema, 1=mild erythema covering most of the test site, 2=moderate erythema with possible presence of mild edema, 3=marked erythema with possible edema, and 4=severe erythema with possible edema, vesiculation, bullae or ulceration. For both materials tested, all scores (10 Induction and 2 Challenge for each of 52 subjects) were 0. In addition, 5 subjects who began the study but discontinued for various reasons not related to the test materials generated scores of only 0 as well. Thus, hydrogel A and hydrogel B showed no dermal irritation or allergic contact sensitization.

Example 44

Speed of Kill of Crosslinked Hydrogels

Hydrogel A was prepared by reacting poly(allylamine hydrochloride), $M_w$ 60,000, with 0.01 mole equivalent (relative to amine groups) of N,N'-bis(ethoxycarbonylmethyl)-D-glucaramide according to Example 32A to give a polymer nominally having 2% of its amine groups crosslinked. Hydrogel B was prepared by reacting poly(allylamine hydrochloride), $M_w$ 60,000, with 0.15 mole equivalent (relative to amine groups) of diethyl L-tartrate according to Example 30A to give a polymer nominally having 30% of its amine groups crosslinked. Hydrogel C was prepared by reacting poly(allylamine hydrochloride), $M_w$ 60,000, with 0.25 mole equivalent (relative to amine groups) of diethyl L-tartrate according to Example 30, except using 0.900 g of poly(allylamine hydrochloride), 0.192 g of sodium hydroxide, and 0.412 mL of diethyl L-tartrate and allowing the reaction to proceed for 88 hours before washing with methanol, to give a polymer nominally having 50% of its amine groups crosslinked.

For each hydrogel, an exposure of *E. coli* to a 100 ppm loading was effected by dispersing 5 mg of hydrogel in 25 mL of 0.6 mM phosphate buffer, stirring overnight, and then adding 25 mL of a culture broth (~$1.0 \times 10^5$ cfu/mL) of *Escherichia coli* ATCC #25922. After 15, 30, 60, 120, 180, and 240 minutes, aliquots of the test mixture were removed and serially diluted 1:10 with TSB in a 96-well microtiter plate. After incubating overnight at 37° C., each plate was scored for microbial growth using a Most Probable Number (MPN) protocol, and log reduction calculated as (mean $\log_{10}$ density of microbes in untreated control samples)−(mean $\log_{10}$ MPN density of microbes in treated samples).

Exposure of *E. coli* to a 10 ppm loading of each hydrogel was effected similarly except using 1 mg of hydrogel in 50 mL of buffer and adding 50 mL of a culture broth (~$1.0 \times 10^5$ cfu/mL) of *Escherichia coli* ATCC #25922.

Results in Table 10 show that all three hydrogels eliminate viable *E. coli* when present at 100 ppm. At 10 ppm loading, it becomes more apparent that the speed of kill of hydrogel A is faster than that of hydrogel B, which is faster than that of hydrogel C.

TABLE 10

Speed of Kill of *E. coli* #25922 by Crosslinked Hydrogels

| | log reduction of cfu/mL | | | | | |
|---|---|---|---|---|---|---|
| | hydrogel A[a] | | hydrogel B[a] | | hydrogel C[a] | |
| t, minutes | 100 ppm | 10 ppm | 100 ppm | 10 ppm | 100 ppm | 10 ppm |
| 15 | 5.40 | 3.09 | 2.39 | 1.69 | 2.39 | 0.99 |
| 30 | 5.40 | 5.36 | 2.39 | 2.78 | 3.48 | 1.69 |
| 60 | 5.40 | 5.40 | 3.23 | 2.78 | 3.48 | 1.83 |
| 120 | 5.40 | 5.40 | 5.40 | 3.95 | 5.36 | 2.08 |
| 180 | 5.40 | 5.40 | 5.40 | 3.79 | 5.40 | 3.09 |
| 240 | 5.40 | 5.40 | 5.40 | 5.40 | 5.40 | 2.78 |

[a]See text of Example 44 for descriptions of hydrogels A, B, and C.

What is claimed is:

1. A crosslinked polymer comprising:
   (A) a linear, branched or cyclic polymeric backbone comprising repeat units that comprise one or more groups selected from: hydrocarbylene groups, heteroatoms, and carbonyl groups; wherein the hydrocarbylene groups are aliphatic or aromatic, linear, branched, or cyclic, and combinations thereof; and
   (B) one or more crosslinking units containing at least one aldaroyl structural unit of Formula I:

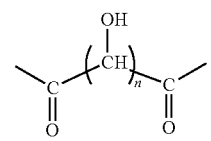

where n is 1-6;

wherein:
(i) the hydrocarbylene groups and heteroatoms of the repeat units are substituted with substituents that comprise one or more of $C_1$-$C_{30}$ hydrocarbylene groups, heteroatoms, and carbonyl carbon groups, and wherein the hydrocarbylene groups of the substituents are aliphatic or aromatic, linear, branched, or cyclic, or combinations thereof; and
(ii) the substituents on the hydrocarbylene groups and heteroatoms of the repeat units comprise one or more of: —X; —OZ; —NZZ'; —N+ZZ'Z"; —COOZ; —COX; —CONZZ'; —CNO; —O—; —NZ—; —N+ZZ'—; —CONZ—; —COO—; —CO—; —OCOO—; —OCONZ—; —N(Z)CONZ'—, —CONH(CH$_2$)$_p$NH$_2$, —Si(ZZ')O—, —(OCH$_2$CH$_2$)$_m$OH, or —(OSi(ZZ'))$_n$OH, and salts thereof, wherein X is a halogen, Z, Z', and Z" are independently hydrogen or $C_1$-$C_{22}$ alkyl, substituted alkyl, aryl, or substituted aryl, and wherein m is 1 to 50, n is 1 to 100, and p is 1 to 12.

2. The crosslinked polymer of claim 1 wherein the repeat units comprise aliphatic hydrocarbylene groups having substituents comprising one or more of C1-C22 aminoalkyl groups, —COOZ, —COX, —CONZZ', or —CONH(CH2)pNH2, and salts thereof.

3. A crosslinked polymer comprising:
   (A) a linear, branched or cyclic polymeric backbone comprising repeat units that comprise one or more groups selected from: hydrocarbylene groups, heteroatoms, and carbonyl groups; wherein the hydrocarbylene groups are aliphatic or aromatic, linear, branched, or cyclic, and combinations thereof; and (B) one or more crosslinking units containing at least one aldaroyl structural unit of Formula I:

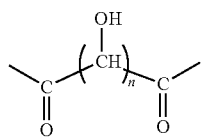

where n is 1-6;

wherein:
(i) the hydrocarbylene groups and heteroatoms of the repeat units are optionally substituted with substituents that comprise one or more of C1-C30 hydrocarbylene groups, heteroatoms, and carbonyl carbon groups, wherein the hydrocarbylene groups of the substituents are aliphatic or aromatic, linear, branched, or cyclic, or combinations thereof; and
(ii) at least one repeat unit is an azahydrocarbylene or salt thereof, comprising a nitrogen atom having one or more terminal aminoalkyl groups or salts thereof as substituents.

4. The crosslinked polymer of either claim 1 or claim 3 wherein at least one repeat unit contains one or more substituents comprising one or more of C1-C22 aminoalkyl groups, optionally substituted with alkyl or aldaroyl groups, or a salt thereof.

5. The crosslinked polymer of claim 1 wherein the polymer is a derivative of polyallylamine, polyallylamine hydrochloride, branched polyethyleneimine, branched polyethyleneimine hydrochloride, poly(acryloyl chloride), poly(methacryloyl chloride), poly[N-(☐-aminoalkyl)acrylamide], polyglycosamine, carboxymethylchitosan, chitosan, chitosan hydrochloride, or a derivative or salt thereof.

6. The crosslinked polymer of claim 1 wherein the aldaroyl moiety in the crosslinking unit is glucaroyl, galactaroyl, mannaroyl, xylaroyl, or tartaroyl.

7. A crosslinked polymer prepared by a process comprising contacting a crosslinking agent with a substrate polymer to form a crosslinked polymer; wherein the crosslinking agent has Formula VI, VII or VIII:

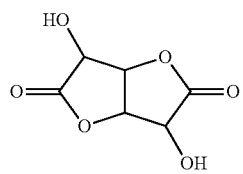

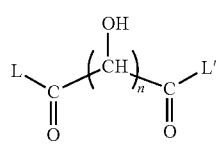

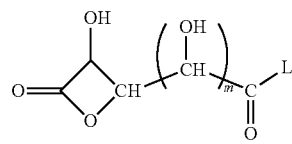

wherein L and L' independently contain a suitable functional group, and n=1-6, m=0-4, and p=1-4;
and the substrate polymer comprises:
A) a linear, branched or cyclic polymeric backbone comprising repeat units that comprise one or more of hydrocarbylene groups, heteroatoms, and carbonyl carbon groups;
wherein the hydrocarbylene are aliphatic or aromatic, linear, branched, or cyclic, or combinations thereof; and
wherein the hydrocarbylene groups and heteroatoms of the repeat units are optionally substituted with substituents that comprise one or more of $C_1$-$C_{30}$ hydrocarbylene groups, heteroatoms, and carbonyl carbon groups, wherein the hydrocarbylene groups of the substituents are aliphatic or aromatic, linear, branched, or cyclic, or combinations thereof; and
B) reactive pendant groups attached to the polymeric backbone, the pendant groups being of the formula -G or —R-G,
wherein G is a nucleophile or electrophile;
wherein R is independently linear, cyclic, or branched alkylene, arylene, or alkarylene groups of 1-22 carbon atoms, optionally substituted with alkyl, aryl, hydroxy, amino, carbonyl, ester, amide, alkoxy, nitrile or halogen, and optionally containing —O—, —Si(ZZ')O—, —(C=O)— or —NZ— linkages, where Z and Z' are independently hydrogen, alkyl, substituted alkyl, alkaryl, substituted alkaryl, aryl, or substituted aryl.

8. The crosslinked polymer of claim 7 wherein the suitable functional group is derived from an amine, hydroxyl, carboxylic acid, ester, urethane, urea, amide, or isocyanate; and G is an epoxide, isocyanate, benzylic halide, amine, acid halide, ester, or amide.

9. The crosslinked polymer of claim 7 wherein L and L' are independently selected from —Y—R, wherein Y is O, NH, or S and R is alkyl, substituted alkyl, alkaryl, substituted alkaryl, aryl, or substituted aryl.

10. The crosslinked polymer of claim 7 wherein L and L' are independently selected from optionally substituted —NHR", —OH, and —C(=O)OR"; and G is selected from —NH2, —C(=O)Cl, —C(=O)OR", or —C(=O)NH—R"—NH2, wherein R" is independently hydrogen or an optionally substituted hydrocarbyl or hydrocarbylene, and wherein n=2-4, m=0-1, and p=2-3.

11. The crosslinked polymer of claim 7 wherein less than 100% of the reactive pendant groups are derivatized to be substantially unreactive to the crosslinking agent, wherein the derivatization is performed either before, during or after contact of the crosslinker with the polymer substrate.

12. The crosslinked polymer of claim 7 wherein the reactive pendant groups are derivatized before the contacting of the crosslinker with the polymer substrate.

13. The crosslinked polymer of claim 7 wherein the reactive pendant groups are derivatized to contain an optionally substituted aliphatic carbon chain with optional —(NZ)—, and —O— linkages, where Z is hydrogen, optionally substituted alkyl or optionally substituted aryl.

14. The crosslinked polymer of claim 7 wherein the reactive pendant groups are derivatized to contain a linear or branched alkyl group of 1-22 carbon atoms, optionally substituted with —O— linkages, and optionally substituted with —NH2, halogen, hydroxyl, or carbonyl groups, or salt thereof.

15. The crosslinked polymer of claim 7 wherein G is —NH2 and the reactive pendant groups are derivatized with a C1-C22 alkyl group.

16. The crosslinked polymer of claim 7 wherein up to about 50% of the reactive pendent groups are derivatized.

17. The crosslinked polymer of claim 7 wherein up to about 20% of the reactive pendent groups are derivatized.

18. The crosslinked polymer of claim 7 wherein the polymeric backbone comprises at least one selected from: —NZ—, —N+ZZ'—, —O—, —C(=O)NZ—, —C(=O)O—, —C(=O)—, —OC(=O)O—, —OC(=O)NZ—, —NHC(=O)NZ—, or —SiZZ'O— linkages, where Z and Z' are independently hydrogen, alkyl, substituted alkyl, aryl, and substituted aryl.

19. The crosslinked polymer of claim 7 wherein the repeat units of the substrate polymer comprise aliphatic hydrocarbylene groups with one or more substituents comprising one or more of aminoalkyl groups, —C(=O)OZ, —C(=O)X, —C(=O)NZZ', or —C(=O)NH(CH₂)nNH2, or salts thereof, where X is halogen, Z and Z' are independently hydrogen, C1-C22 alkyl, substituted alkyl, aryl, or substituted aryl, and n=1-12.

20. The crosslinked polymer of claim 7 wherein substituents on the repeat units are one or more of —X, —O(Z), —N(ZZ'), —N+(ZZ'Z"), —C(=O)OZ, —C(=O)X, —C(=O)NZZ', —C=N=O, —O—, —N(Z)—, —N+(ZZ')—, —C(=O)N(Z)—, —C(=O)O—, —C(=O)—, —OC(=O)O—, —OC(=O)N(Z)—, —N(Z)C(=O)N(Z')—, —C(=O)NH(CH2)pNH2, —Si(ZZ')O—, —(OCH2CH2)mOH, or —(OSi(ZZ'))nOH, or salts thereof, wherein X is a halogen, Z, Z', and Z" are independently hydrogen or C1-C22 optionally substituted alkyl or aryl, and wherein m is 1 to 50, n is 1 to 100, and p is 1 to 12.

21. The crosslinked polymer of claim 7 wherein the repeat units contain substituents comprising one or more of C1-C22 aminoalkyl groups, optionally substituted with alkyl or aldaroyl groups, or salts thereof.

22. The crosslinked polymer of claim 7 wherein at least one repeat unit is an azahydrocarbylene or salt thereof, comprising a nitrogen atom having one or more terminal aminoalkyl groups or salts thereof as substituents.

23. The crosslinked polymer of claim 7 wherein the substrate polymer comprises polyallylamine, polyallylamine hydrochloride, branched polyethyleneimine, branched polyethyleneimine hydrochloride, poly(acryloyl chloride), poly(methacryloyl chloride), poly[N-(☐-aminoalkyl)acrylamide], polyglycosamine, carboxymethylchitosan, chitosan, chitosan hydrochloride, or a derivative or salt thereof.

24. The crosslinked polymer of claim 7 wherein the crosslinking agent is derived from an aldaric acid, aldarolactone, aldarodilactone, aldarolactone ester, aldaric acid monoester, aldaric acid diester, or aldaramide, or salts thereof.

25. The crosslinked polymer of claim 7 wherein the crosslinking agent is derived from glucaric acid, galactaric acid, mannaric acid, xylaric acid or tartaric acid.

26. The crosslinked polymer of claim 7 wherein the crosslinking agent is of the Formulae IX, X, XI, XII:

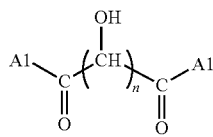

IX

-continued

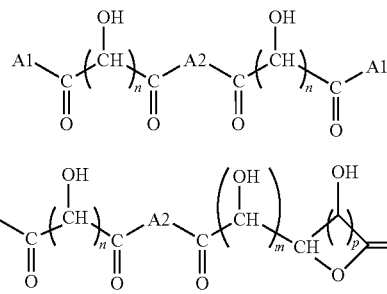

X

XI

XII wherein A1 is independently selected from:

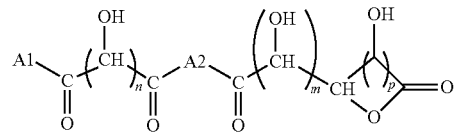

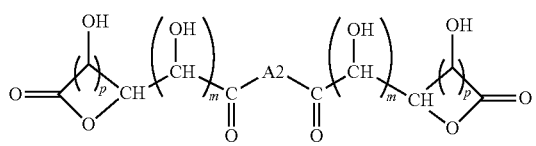

and salts thereof;

wherein R5 and R7 are independently aliphatic or aromatic hydrocarbylene groups, linear or cyclic, optionally substituted with alkyl, aryl, hydroxy, amino, carbonyl, carboxyl, ester, amide, alkoxy, nitrile or halogen, or slats thereof, and optionally containing —O—, —Si(ZZ')O—, —(C=O)— or —NZ— linkages, where Z and Z' are independently hydrogen, alkyl, substituted alkyl, alkaryl, substituted alkaryl, aryl, or substituted aryl; and R6 is hydrogen or a 1-22 carbon alkyl group.

27. The crosslinked polymer of claim 26 wherein R5 and R7 are independently optionally substituted aliphatic carbon chains with optional —(NZ)— or —O— linkages, wherein Z is hydrogen, optionally substituted alkyl or optionally substituted aryl.

28. The crosslinked polymer of claim 26 wherein R5 and R7 are independently linear, cyclic, or branched alkylene groups of 1-10 carbon atoms, optionally substituted with —O— linkages, and optionally substituted with —NH2 groups, or salts thereof.

29. The crosslinked polymer of claim 26 wherein R7 is —[(CH2)1-21]-; —CH(CH3)-; —CH(isopropyl)-; —CH(isobutyl)-; —CH(CH(CH3)CH2CH3)-; —CH(CH2OH)—; —CH(CH2CH2SCH3)-; —CH(CH(OH)CH3)-; —CH(CH2C6H5)-; —CH(CH2C6H4OH)—; —CH(CH2CONH2)-; or —CH(CH2CH2CONH2)-;

and

R5 is —[(CH2)2-22]-; —[(CH2)0-6(C6H10)(CH2)0-6]-; —[(CH2)0-6C6H4(CH2)0-6]-; —[CH2CH2(OCH2CH2)1-21]-; —[CH2CH(CH3)[OCH2CH(CH3)]1-21]-; —(CH2CH2NH)1-22CH2CH2-; —[CH2CH(CH3)[OCH2CH(CH3)]x(OCH2CH2)y[OCH2CH(CH3)]z]- wherein x+y+z=2-50;
-[CH2CH2(OCH2CH2)x[OCH2CH(CH3)]y(OCH2CH2)z]- wherein x+y+z=2-50;
—[CH(CH3)CH2O]xCH2C(Z')(CH2[OCH2CH(CH3)y-)CH2[OCH2CH(CH3)]z- wherein x+y+z=2-10 and Z' is H, methyl or ethyl;

—[CH(CH3)CH2O]xCH2CH([OCH2CH(CH3)]y—)CH2[OCH2CH(CH3)]z- wherein x+y+z=3-100; or

—CH2CH2CH2CH2[CH(NH2)CONHCH2CH2CH2CH2]0-10CH(COYR)—, or salts thereof, wherein Y is O or NH, and R is a C1-C22 optionally substituted alkyl, aryl, or alkaryl.

30. The crosslinked polymer of claim 26 wherein about 0.0005 to about 0.5 molar equivalents of crosslinking agent are used per reactive pendant group.

31. The crosslinked polymer of claim 26 wherein about from about 0.005 to about 0.5 molar equivalents of crosslinking agent are used per reactive pendant group.

32. The crosslinked polymer of claim 26 wherein 0.01 to 0.25 molar equivalents of the reactive pendant groups are derivatized.

* * * * *